(12) United States Patent
Yamashita et al.

(10) Patent No.: US 7,355,702 B2
(45) Date of Patent: Apr. 8, 2008

(54) CONFOCAL OBSERVATION SYSTEM

(75) Inventors: Yusuke Yamashita, Tokyo (JP); Kei Tsuyuki, Tokyo (JP); Tatsuo Nakata, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/153,635

(22) Filed: Jun. 15, 2005

(65) Prior Publication Data

US 2005/0280818 A1   Dec. 22, 2005

(30) Foreign Application Priority Data

Jun. 21, 2004 (JP) ............................. 2004-182552
Jul. 7, 2004 (JP) ............................. 2004-200735

(51) Int. Cl.
*G01J 3/44* (2006.01)

(52) U.S. Cl. .................................................. 356/301
(58) Field of Classification Search ................. 356/301
See application file for complete search history.

(56) References Cited

U.S. PATENT DOCUMENTS

| | | | | |
|---|---|---|---|---|
| 5,034,613 A | * | 7/1991 | Denk et al. | 250/458.1 |
| 5,225,923 A | * | 7/1993 | Montagu | 359/199 |
| 6,094,300 A | | 7/2000 | Kashima et al. | |
| 6,437,913 B1 | * | 8/2002 | Kishi | 359/389 |
| 6,855,941 B1 | | 2/2005 | Tomioka | |
| 7,009,171 B2 | * | 3/2006 | Sasaki | 250/234 |

FOREIGN PATENT DOCUMENTS

| | | |
|---|---|---|
| JP | 10-206742 A | 8/1998 |
| JP | 11-326775 A | 11/1999 |
| JP | 2003-195174 A | 7/2003 |

* cited by examiner

*Primary Examiner*—Tarifur Chowdhury
*Assistant Examiner*—Isiaka O Akanbi
(74) *Attorney, Agent, or Firm*—Frishauf, Holtz, Goodman & Chick, P.C.

(57) ABSTRACT

A confocal observation system, comprising, an image acquisition unit for acquiring optical cross sectional images of a three-dimensional specimen, a three-dimensional image construction unit for constructing a three-dimensional image from the optical cross sectional images acquired by the image acquisition unit, a specification unit for specifying a desired three-dimensional region in the three-dimensional image constructed by the three-dimensional image construction unit, and a region acquisition unit for acquiring a cross sectional region to be irradiated with excitation light or stimulation light based on the three-dimensional region specified by the specification unit, wherein the excitation light or the stimulation light irradiates a region in the three-dimensional specimen corresponding to the cross sectional region acquired by the region acquisition unit.

12 Claims, 18 Drawing Sheets

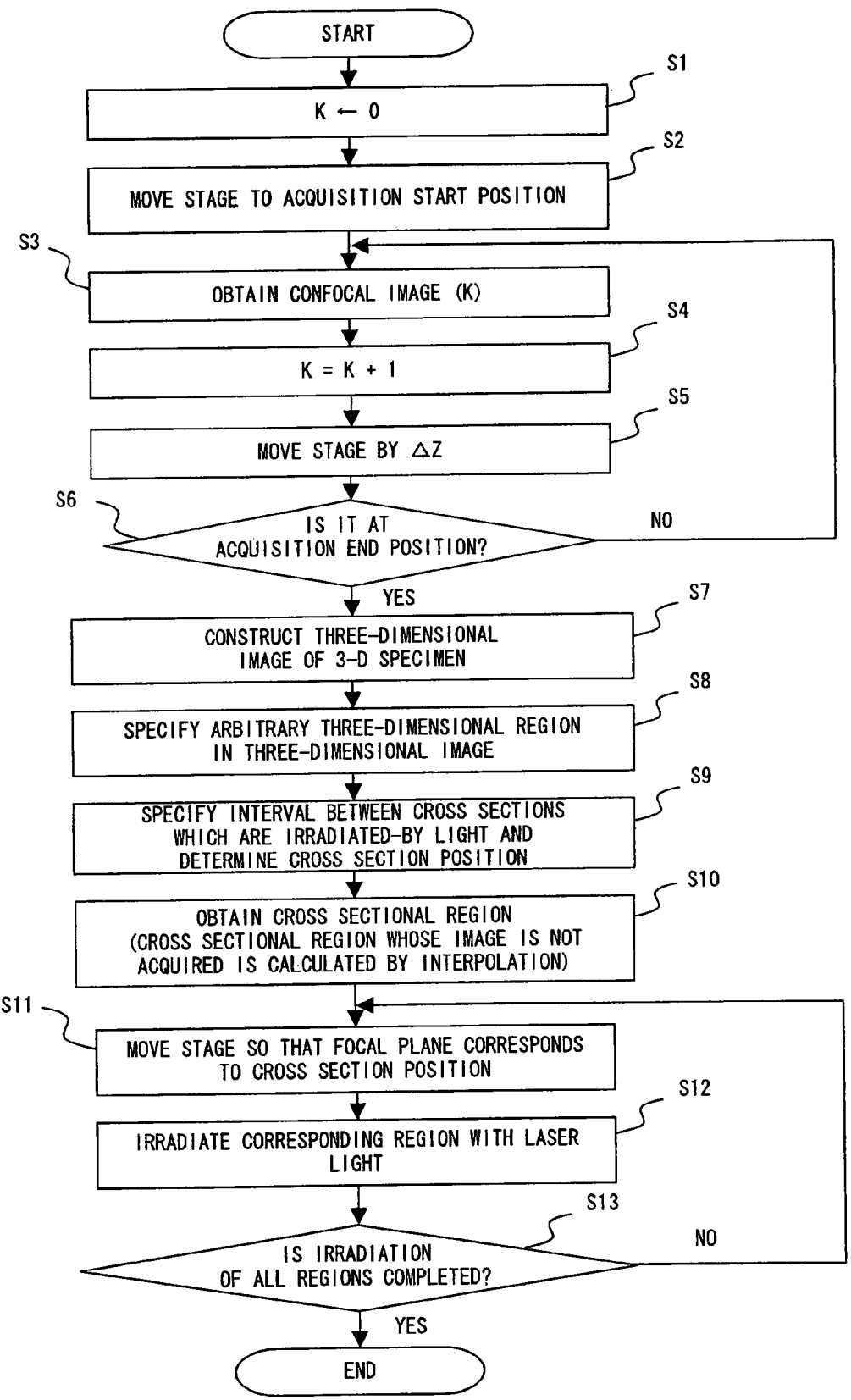
F I G. 3

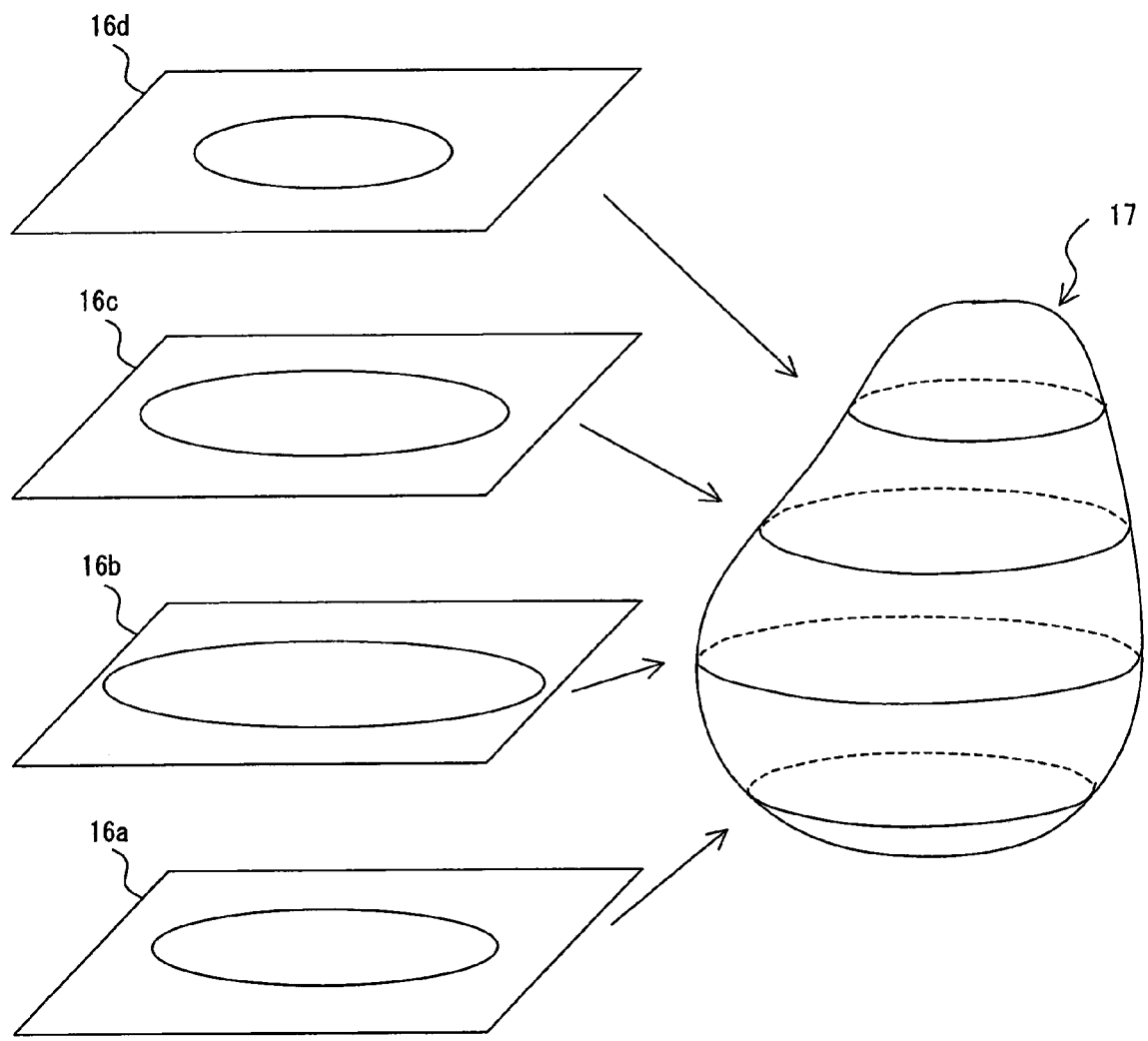
F I G. 4

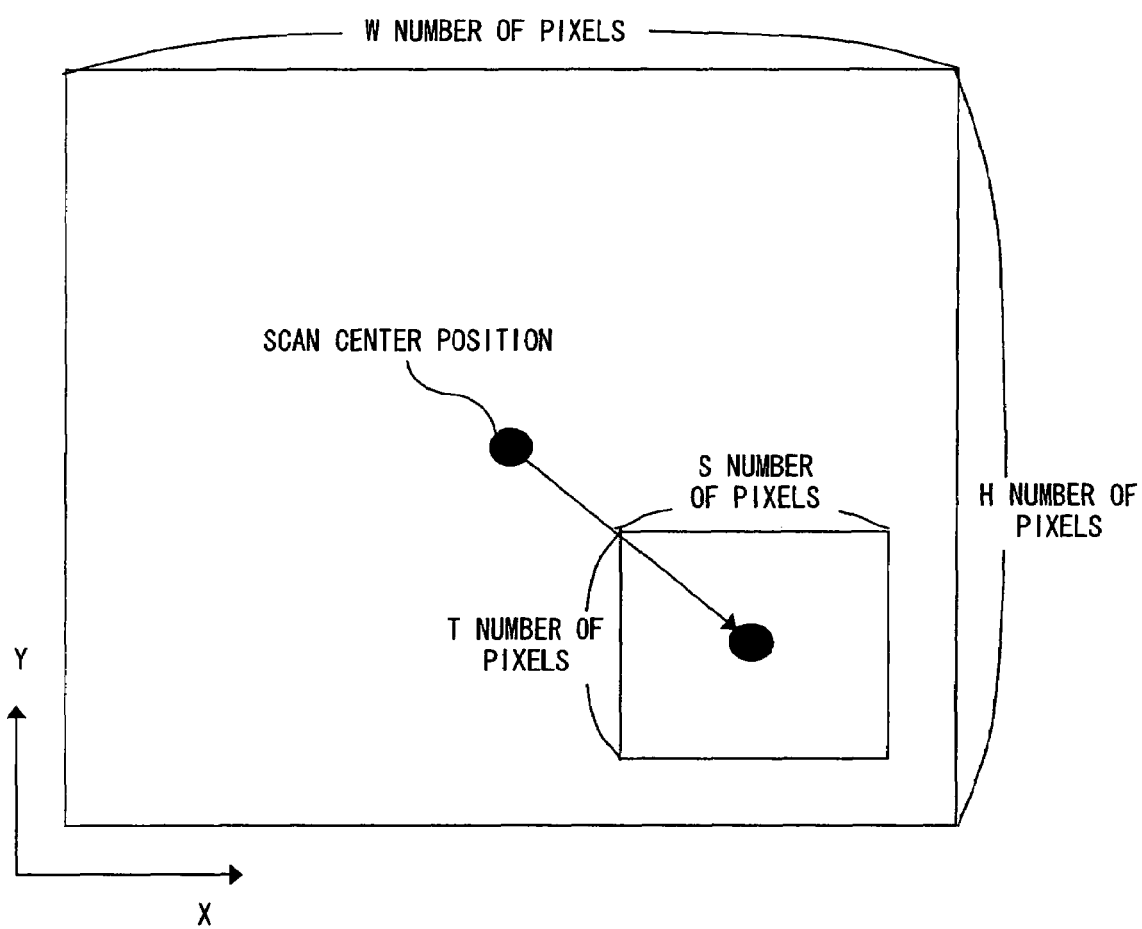
F I G. 17

CONFOCAL OBSERVATION SYSTEM

CROSS REFERENCE TO RELATED APPLICATIONS

This application is based upon and claims the benefit of priority from the prior Japanese Patent Applications No. 2004-182552, filed Jun. 21, 2004; and No. 2004-200735, filed Jul. 7, 2004, the entire contents of which are incorporated herein by reference.

BACKGROUND OF THE INVENTION

1. Field of the Invention

The present invention relates to a confocal observation system, and more particularly, to a confocal observation system such as a microscope or an endoscope including scanning optical systems.

2. Description of the Related Art

The confocal scanning microscope is a microscope which two-dimensionally scans a sample by means of light such as that of a laser beam or the like, detects, by an optical detector, the reflected light, the transmitted light or the fluorescence from the sample via an optical system including an objective lens, and obtains two-dimensional intensity information of the reflected light, the transmitted light or the fluorescence.

Also, in the confocal scanning microscope, the fluorescence image of the sample can be observed by displaying the above intensity information as a two-dimensional distribution of the intensity on a CRT or the like. The confocal scanning microscope such as above suppresses the scatted light which does not come from the measured point by combining a point light source such as a laser beam light source and a pinhole and by irradiating the sample with pin point accuracy. Also, by using the pinhole as a spatial filter provided in front of the optical detector which images the light existing on the plane including the measured point around the pinhole, the light from the plane which has been shifted to the optical axis direction is prevented from passing through the pinhole.

According to the above method, an optically sliced image can be obtained.

Also, in the confocal scanning microscope, the sample is two-dimensionally scanned by a spot beam and the focal point is moved by a prescribed pitch in the Z axis direction which is the optical axis direction so that a plurality of the sliced images are obtained, accordingly, sliced images of a three-dimensional space (referred to as a Z-stack image, hereinafter) can be obtained as a result.

Additionally, when multiphoton absorption is caused by using a component which emits pulsed laser beam or the like as the laser light source, only the portion of the specimen lying in the focal plane will be excited. Accordingly, even when the pinhole is not provided, only information about the focal plane of the specimen will be obtained.

Also, when another scanning optical system is provided in addition to the optical system for acquiring the image, the irradiation by the laser beam for photostimulation and the acquisition of the image can be conducted separately.

When three-dimensional information of the biological sample is to be obtained by the confocal scanning microscope such as that above, the three-dimensionally scanned region is searched and determined by moving a stage which carries the sample while monitoring the two-dimensional image displayed on a CRT or the like.

As a method of determining the three-dimensionally scanned region, a technique is disclosed in Japanese Patent Application Publication No. 2003-195174. In this technique, an example in which dendritic information of a cell is obtained is employed. First, the laser beam irradiates the 3-D sample and a Z-stack image of the sample is obtained.

Next, by using at least two of the two-dimensional data made by reflecting the obtained Z-stack image onto the XY plane, the two-dimensional data made by reflecting the obtained three-dimensional image onto the YZ plane and the two-dimensional data made by reflecting the obtained three-dimensional image onto the ZX plane, the curve data for the basic path of the nerve cell or the like for example included in the sample is obtained from the two-dimensional data.

By scanning the sample in accordance with the curve data for the basic path, the three-dimensional information of the nerve cell or the like in the sample can be obtained.

Also, in the document of U.S. Pat. No. 6,855,941 B1, a technique for a multiphoton excitation laser microscope which requires adjustment for preparing suitable observation conditions, in which the simple setting of conditions is realized by the arrangement of the optical members is disclosed. Also, in the document of U.S. Pat. No. 6,094,300, a method in which another scanning optical system in addition to the detecting optical system is provided so that the photostimulation is caused separately from the observation position is proposed.

SUMMARY OF THE INVENTION

The confocal observation system according to a first aspect of the present invention is the system, comprising an image acquisition unit for acquiring optical cross sectional images of a three-dimensional specimen, a three-dimensional image construction unit for constructing a three-dimensional image from the optical cross sectional images acquired by the image acquisition unit, a specification unit for specifying a desired three-dimensional region in the three-dimensional image constructed by the three-dimensional image construction unit, and a region acquisition unit for acquiring a cross sectional region which is to be irradiated with excitation light or stimulation light based on the three-dimensional region specified by the specification unit, wherein the excitation light or the stimulation light irradiates a region in the three-dimensional specimen corresponding to the cross sectional region acquired by the region acquisition unit.

The confocal observation system according to a second aspect of the present invention is the system according to the first aspect, wherein the specification unit specifies a plurality of the desired three-dimensional regions in the three-dimensional image constructed by the three-dimensional image construction unit, the region acquisition unit acquires a cross sectional region which is to be irradiated with excitation light or stimulation light, based on the plurality of the three-dimensional regions specified by the specification unit, and the cross sectional region based on the plurality of the three-dimensional regions acquired by the region acquisition unit is scanned at a high resolution by the irradiation of the excitation light or the stimulation light.

BRIEF DESCRIPTION OF THE DRAWINGS

FIG. 3 is a flowchart of a process of operations of the confocal laser microscope device according to the embodiment 1;

FIG. 4 shows a specific example when a process flow according to the embodiment 1 is executed;

FIG. 17 explains the detail scan region calculation in the embodiment 3; and

DESCRIPTION OF THE PREFERRED EMBODIMENTS

Hereinafter, the embodiments of the present invention will be explained with references to the drawings.

Embodiment 1

Figure 1:
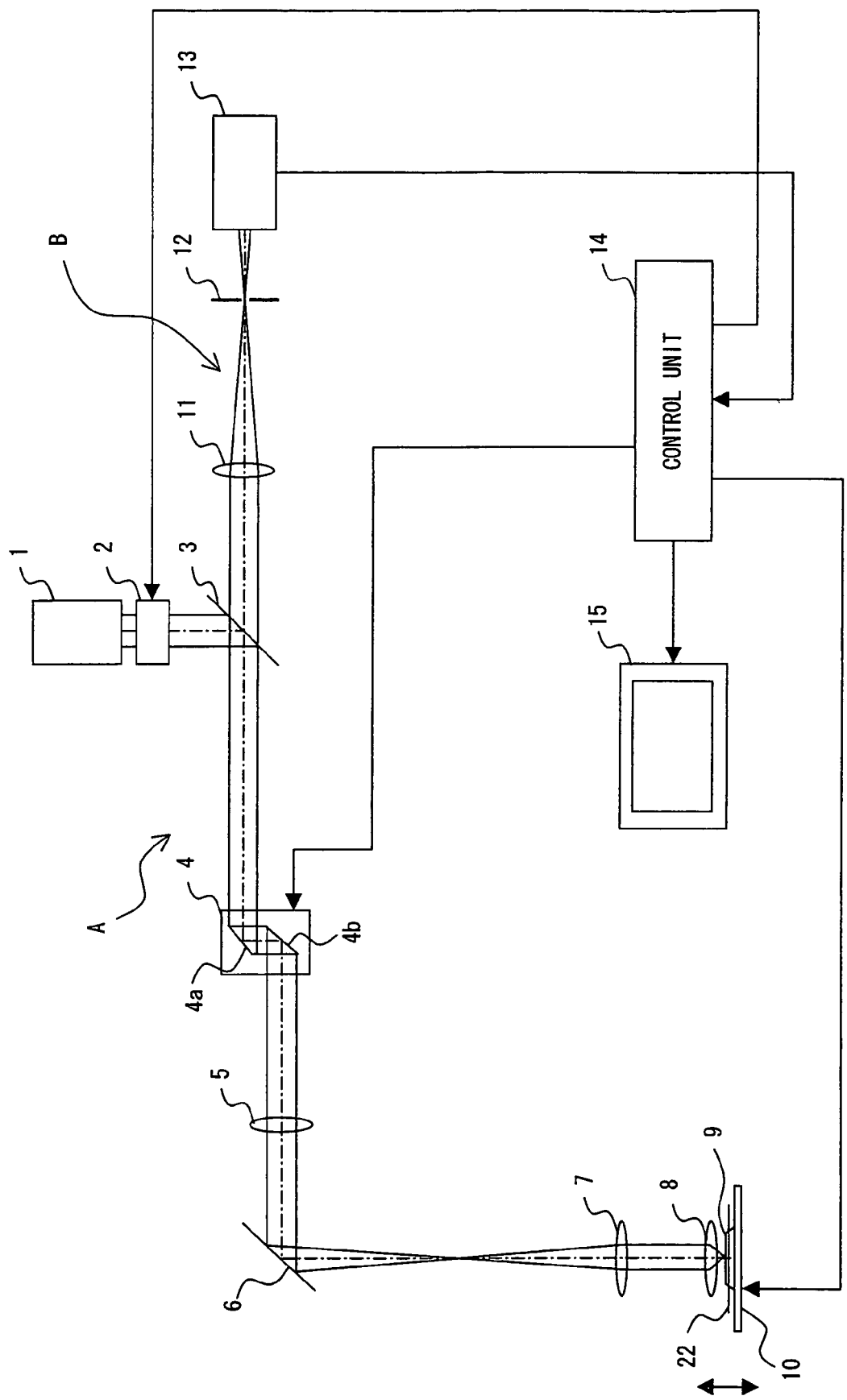
FIG. 1 shows a configuration of a confocal laser microscope device as a confocal observation system according to an embodiment 1.

FIG. 1 shows a configuration of a confocal laser microscope device as a confocal observation system according to an embodiment 1 of the present invention.

As shown in FIG. 1, the present device comprises a laser light source 1 for emitting an irradiating laser beam, a laser control unit 2 for adjusting the wavelength and intensity of the laser beam emitted by the laser light source 1, a dichroic mirror 3, an optical scanning unit 4 for deflecting the laser beam in the two-dimensional directions (X and Y directions) which includes two optical scanners 4a and 4b, a relay lens 5, a reflection mirror 6, an imaging lens 7, an objective lens 8, a stage 10 movable in the optical axis direction (Z axis direction) on which a 3-D specimen 9 is set, a lens 11, a pinhole 12 provided at the conjugate position with the focal position of the objective lens 8, a photoelectric conversion unit 13 for converting the light which has passed through the pinhole 12 into electric signals, a control unit 14 for controlling the entire operation of the present device, and a display unit 15.

In the present device, an optical system comprising the laser light source 1, the laser control unit 2, the dichroic mirror 3, the optical scanning unit 4, the relay lens 5 and the reflection mirror 6 is referred to as the scanning optical system A, and an optical system comprising the lens 11 and the pinhole 12 is referred to as an detecting optical system B.

In the present device, the laser beam emitted from the laser light source 1 is adjusted to laser beam having an arbitrary wavelength and laser intensity by the laser controlling unit 2 controlled by the control unit 14, thereafter, is reflected by the dichroic mirror 3, is guided to the optical scanning unit 4 controlled by the control unit 14, and is deflected in an arbitrary direction. The laser beam which has been deflected is transmitted through the relay lens 5, thereafter, is reflected by the reflection mirror 6, and reaches, through the imaging lens 7 and the objective lens 8, the 3-D specimen 9 mounted on the stage 10 movable in the optical axis direction by being controlled by the control unit 14. Accordingly, two-dimensionally deflects the laser beam by the optical scanning unit 4, the laser beam is two-dimensionally scanned on the focal plane 22 of the 3-D specimen 9. Additionally, the focal plane 22 is the plane including the focal position of the objective lens 8 which is perpendicular to the optical axis direction.

To the contrary, the fluorescence or the reflected light from the focal plane 22 which is generated by the laser beam having reached the 3-D specimen 9 as described above is transmitted through the objective lens 8, the imaging lens 7, the reflection mirror 6, the relay lens 5 and the optical scanning unit 4 along the same path as the above laser beam and in the opposite direction. Then, by the dichroic mirror 3, only the light whose wavelength is selected from the light having been transmitted through the optical scanning unit 4 reaches the detecting optical system B. In the detecting optical system B, the above light whose wavelength is selected is transmitted through the lens 11, and only the light on the focal plane 22 in the 3-D specimen 9 of the light having been transmitted through the lens 11 is selected and reaches the photoelectric conversion unit 13.

Figure 2:
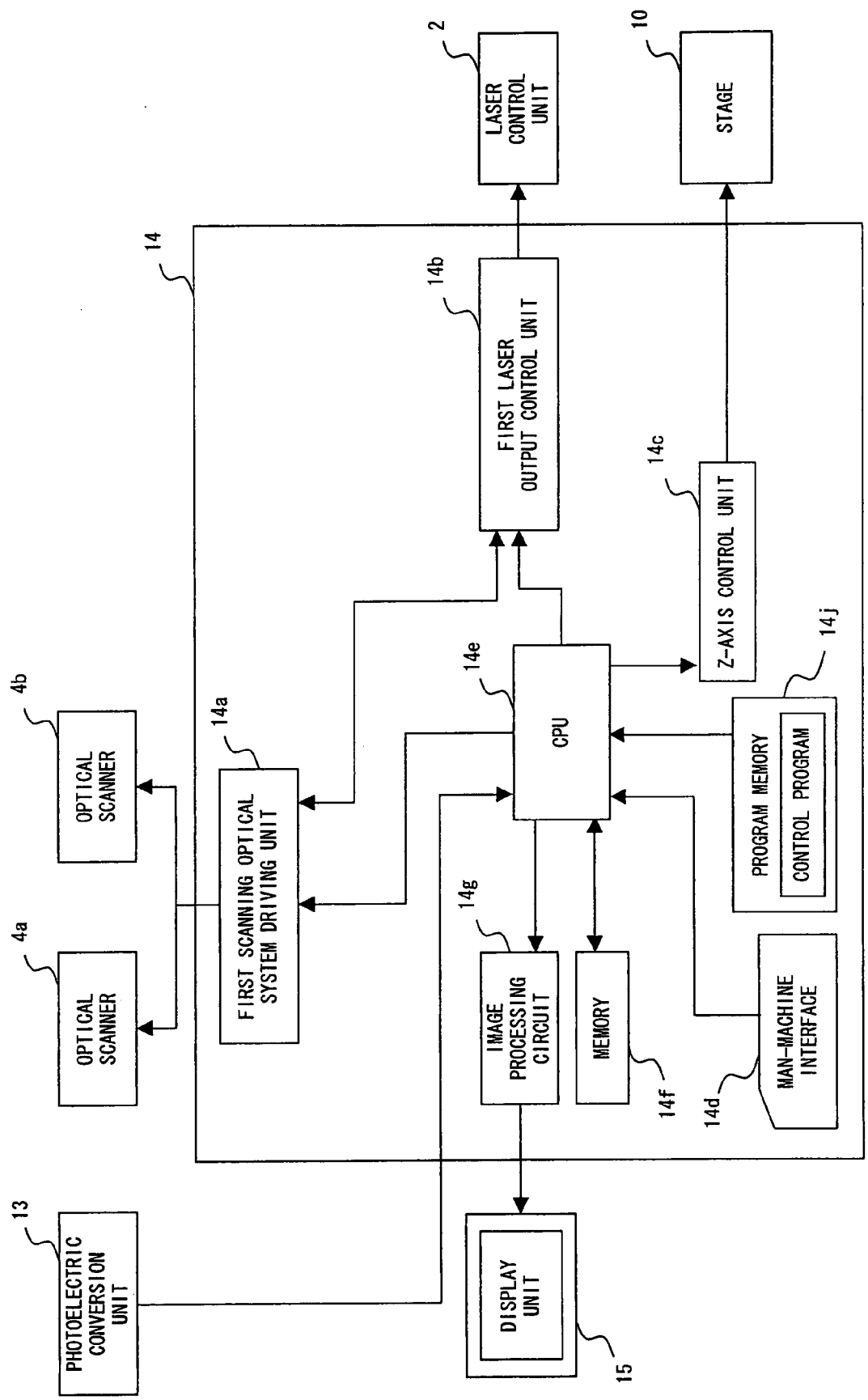
FIG. 2 is a block diagram showing a configuration of a control unit according to the embodiment 1.

FIG. 2 is a block diagram for showing a configuration of the control unit 14 which conducts control or the like of driving the scanning optical system A and displaying the signal from the detecting optical system B as an image.

In FIG. 2, the present unit 14 comprises a first scanning optical system driving unit 14a for driving the optical scanners 4a and 4b, a first laser output control unit 14b for controlling the laser control unit 2, a Z-axis control unit 14c for controlling the movement of the stage 10, a man-machine interface 14d for accepting various inputs by users, program memory 14j for storing a control program, a CPU 14e for controlling the operations of the present device in its entirety including the A/D conversion of the electric signal obtained by the photoelectric conversion unit 13 and the like, memory 14f for storing the electric signal A/D converted by the CPU 14e as an optical cross sectional image, and an image processing circuit 14g for conducting a prescribed image process on the optical cross sectional image stored in the memory 14f upon displaying the image on the display unit 15.

Next, the operations conducted upon the irradiation by the excitation light of an arbitrary three-dimensional region in the 3-D specimen 9 as the operations by the above confocal laser microscope device will be explained.

In the present device, the 3-D specimen 9 can be three-dimensionally observed by continuously capturing the optical cross sectional images of the 3-D specimen 9 while moving the stage 10 in the optical axis direction, and by a three-dimensional construction from the captured Z-stack image. Capturing the Z-stack image and the three-dimensional construction is conducted in the following manner.

First, the optical cross sectional image is obtained at the reference position where Z=0. Thereafter, the optical cross sectional images of the 3-D specimen 9 are continuously captured while changing the positions along the Z axis direction (referred to as "Z position" hereinafter) by driving the stage 10, and the captured optical cross sectional images are stored in the memory 14f together with the information about the Z positions. Then, the optical cross sectional images stored in the memory 14f as above are superimposed on each other along the Z axis on the display unit 15 based on the corresponding Z position information, and a thickness is given to each optical cross sectional image along the Z axis direction in accordance with a prescribed condition. Thereby, the three-dimensional image can be constructed.

FIG. 3 is a flowchart of a process of operations of the above confocal laser microscope device. In FIG. 3, steps S1 to S7 specify processes of capturing the Z-stack image and the three-dimensional construction.

First, the symbol "k" specifying the value corresponding to the Z position (the cross section position) is set to 0 (S1), and the stage 10 is moved to the image acquisition start position (S2) which is set beforehand. Thereby, the focal position is set to the original position.

Next, the optical scanning unit 4 conducts a two-dimensional scan, obtains the confocal image (k) which is the optical cross sectional image, and stores the obtained confocal image in the memory 14f together with the information of the Z position at the time of the current acquisition (S3). Additionally, the confocal image (k) means the optical cross sectional image at the Z position corresponding to "k".

Next, "k" is set to "k+1" (S4), and the stage 10 is moved by a prescribed distance ΔZ (S5). Then, it is determined whether or not the Z position of the stage 10 is the image acquisition end position which is set beforehand (S6). When the result of the above determination is No, the process returns to S3. As above, the above described processes of the steps S3 to S5 are repeated until the Z position of the stage 10 corresponds to the image acquisition end position.

To the contrary, when the result of the determination in the step S6 is Yes, the optical cross sectional images stored in the memory 14f are subsequently superimposed along the Z axis based on the corresponding Z position information, and thereby, the three-dimensional image of the 3-D specimen 9 is constructed (S7). Thereafter, the constructed image is displayed on the display unit 15.

Subsequently, an arbitrary three-dimensional region in the three-dimensional image displayed on the display unit 15 is specified in accordance with instructions of the user given via the man-machine interface 14d (S8).

Next, in accordance with the instructions given by the user via the man-machine interface 14d, the interval between the cross sections which are irradiated by the excitation light (Z interval) is specified, and based on the cross section interval and the three-dimensional region specified in the step S8, the plurality of cross section positions in the 3-D specimen 9 which are irradiated by the excitation light are determined (S9). Additionally, in the present embodiment, the plurality of cross section positions with uniform intervals are determined in this step S9.

Next, when there is a cross section position which is equal to the cross section position of the optical cross sectional image obtained in the step S3 among the above plurality of determined cross section positions, the cross sectional region which is the cross sectional region in the three-dimensional region being specified in the step S8 which corresponds to the above equal cross section position is obtained based on the optical cross sectional image at the above equal cross section position, and, when there is a cross section position which is not equal to the cross section position of the optical cross sectional image obtained in the step S3 among the above plurality of the determined cross section positions, the cross sectional region which is the cross sectional region in the three-dimensional region being specified in the step S8 which corresponds to the above not equal cross section position is calculated by interpolation based on the optical cross sectional image obtained in the step S3 (S10). Additionally, a cross sectional region calculated by this interpolation is referred to as a virtual cross sectional region.

Next, the stage 10 is moved so that the focal plane 22 corresponds to one of the plurality of the cross section positions determined in the step S9 (S11), and the laser beam irradiates the region corresponding to the cross sectional region obtained in the step S10 or a region corresponding to a virtual cross sectional region calculated by interpolation in step S10 at the position of the above one cross section position as excitation light for photostimulation and photobleaching (S12).

Subsequently, it is determined whether or not the laser beam irradiates the sample at all the cross section positions among the plurality of the cross section positions determined in the step S9 (S13). When the result of the above determination is No, the process returns to the step S11, and again executes the processes of the steps S11 and S12 regarding one of the cross section positions which is not irradiated by the laser beam. When the result of the determination in the step S13 is Yes, it is recognized that the laser beam irradiates the sample at all the cross section positions so that the preset flow is ended.

Figure 5:
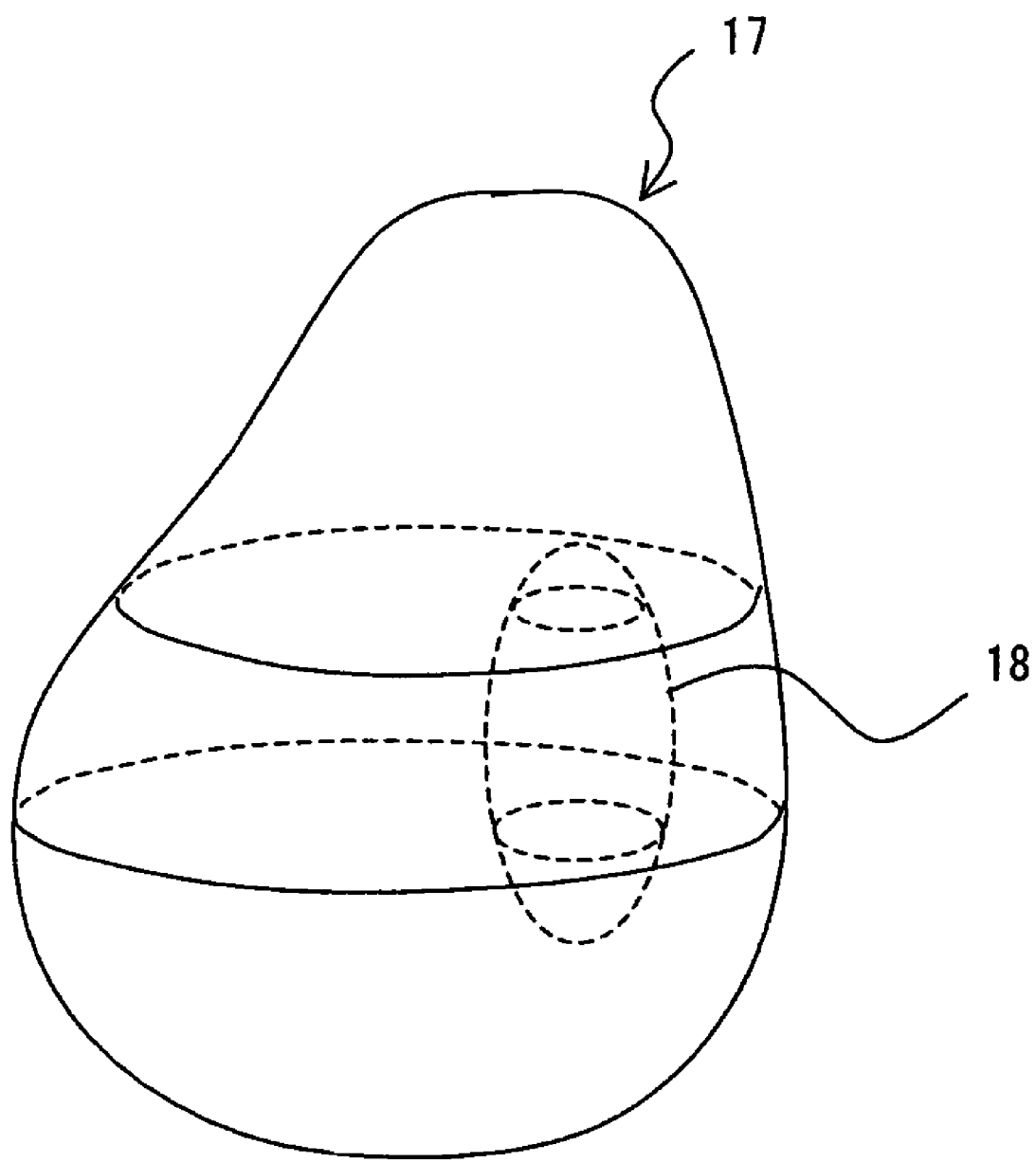
FIG. 5 shows a specific example when a process flow according to the embodiment 1 is executed.
Figure 6:
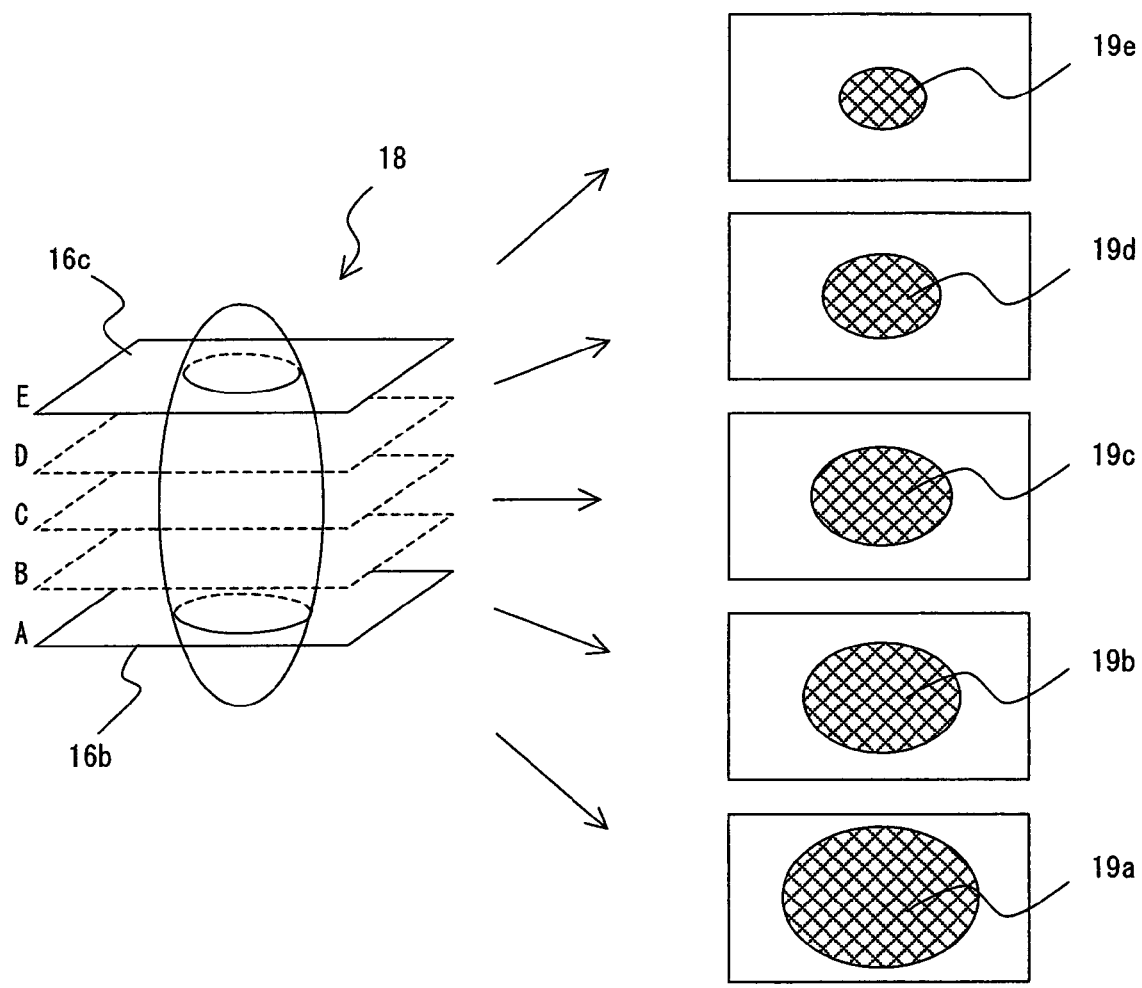
FIG. 6 shows a specific example when a process flow according to the embodiment 1 is executed.

FIG. 4, FIG. 5, and FIG. 6 respectively show specific examples when the present flow is executed.

FIG. 4 shows an example of the optical cross sectional images and the three-dimensional image of the 3-D specimen 9 constructed based on the optical cross sectional images, obtained by the processes of the steps S1 to S7.

In the example of FIG. 4, four optical cross sectional images 16a, 16b, 16c and 16d are obtained and a three-dimensional image 17 of the 3-D specimen 9 is constructed based on the above four optical cross sectional images 16.

FIG. 5 shows an example of the three-dimensional region specified by the process of the step S8 in the three-dimensional image 17 shown in FIG. 4.

In FIG. 5, an example in which a three-dimensional region 18 is specified by the instruction of the user is shown.

FIG. 6 shows the cross section positions determined by the process in the step S9 in the three-dimensional region 18 shown in FIG. 5, and the cross sectional regions and the virtual cross sectional regions obtained by the process in the step S10.

In the example of FIG. 6, the interval between the cross sections is specified in accordance with the instructions of the user, the cross section positions A, B, C, D and E with the uniform intervals are determined (shown as the cross section positions on the display unit 15 in this example), and cross sectional regions in the three-dimensional region 18 19a, 19b, 19c, 19d and 19e in respective cross section positions are obtained.

The cross section position A is equal to the cross section position of the optical cross sectional image 16b, and the cross section position E is equal to the cross section position of the optical cross sectional image 16c. Accordingly, the cross sectional region 19a is obtained from the optical cross sectional image 16b, and the cross sectional region 19e is obtained from the optical cross sectional image 16c. To the contrary, none of the cross section positions B, C or D is equal to a cross section position in the optical cross sectional image 16 so that the cross sectional regions 19b, 19c and 19d are calculated by the interpolation based on the optical cross sectional images 16b and 16c between which there are the regions 19b, 19c and 19d.

When the cross sectional regions 19a, 19b, 19c, 19d and 19e in the cross section positions A, B, C, D and E are obtained, the processes in the steps S11 to S13 are executed, and the laser beam irradiates all the regions corresponding to respective cross sectional regions 19.

As above, according to the present embodiment, by specifying an arbitrary three-dimensional region in the three-dimensional image of the 3-D specimen 9 in accordance with the instruction by the user, photostimulation and photobleaching can be accurately conducted over the corresponding region in the 3-D specimen 9, and the behavior analysis after the photostimulation of the 3-D specimen 9 can be accurately conducted. Additionally, when the number of the optical cross sectional images obtained upon the construction of the three-dimensional image of the 3-D specimen 9 is reduced, the total amount of the laserbeam irradiating the 3-D specimen upon the acquisition can be reduced so that unnecessary photostimulation and photobleaching can be avoided as much as possible.

In addition, in the present embodiment, the confocal laser microscope device employs the configuration in which the focal plane 22 is moved by moving the stage 10 along the optical axis direction. However, a configuration can be employed in which the focal plane 22 is moved by moving the objective lens 8 along the optical axis directions as well.

Also, in the present embodiment, the interval between the cross sections irradiated by the excitation light is specified in accordance with the instructions of the user in the step S9 of FIG. 3. However, this specification can be automatically made by the present device too.

Also, in the step S9, the cross section positions are determined based on the interval between the cross sections irradiated by the excitation light in accordance with the instructions of the user. However, in stead of the above configuration, the cross section positions can be determined by arbitrary points specified in the three-dimensional region by the user.

Figure 7:
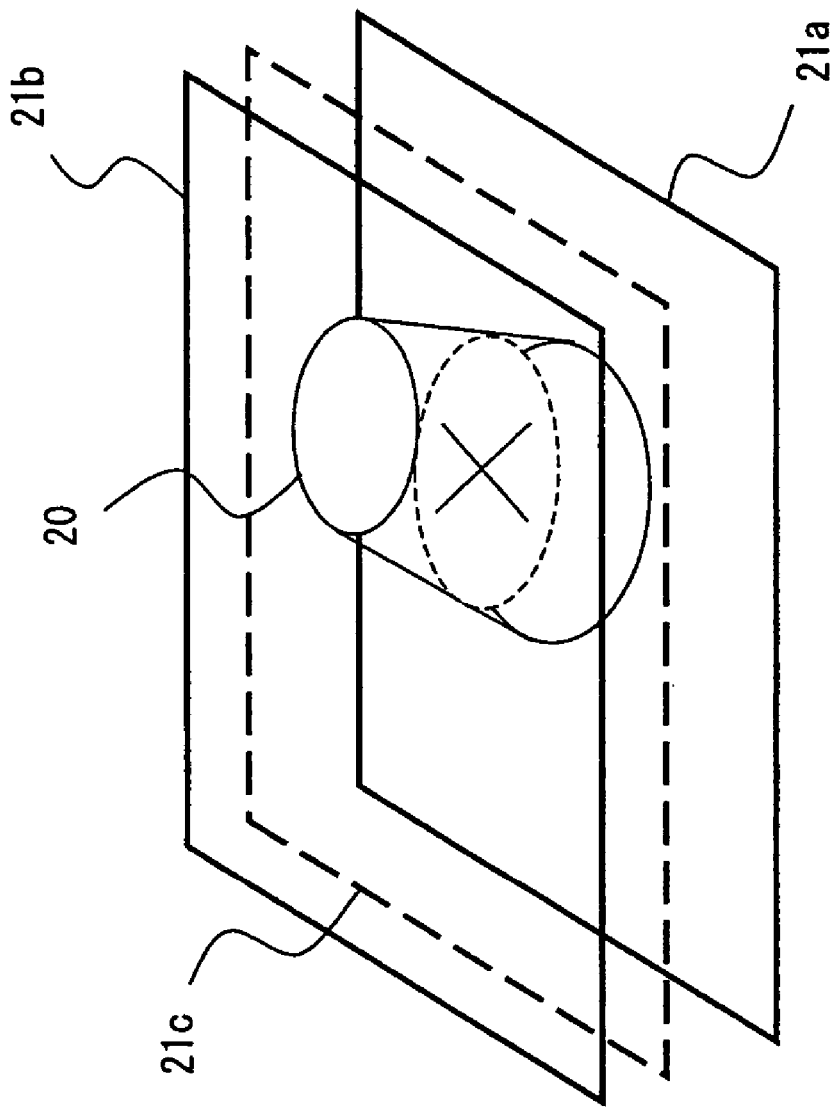
FIG. 7 shows an example in which cross section positions are determined by an arbitrary point in the three-dimensional region specified by a user.

FIG. 7 shows an example in which the cross section positions are determined by the arbitrary point specified by the user in step S9.

In FIG. 7, a three-dimensional region 20 is a part of the three-dimensional region specified in the step S8, and cross sections 21a and 21b expressed by solid lines are the cross sections whose cross section positions are both equal to those of the optical cross sectional images obtained in the step S3.

The user specifies a desired point (indicated by "X" in FIG. 7) within the three-dimensional region 20. When the cross section position of the above specified point is not equal to that in the optical cross sectional image obtained in the step S3, the cross section position corresponding to the cross section including the specified point is obtained in the following manner.

It is noted that the z-coordinate of the cross section 21a on the display unit 15 is z1, and the Z position of the stage 10 corresponding to the z1 is Z1. Also, the z-coordinate of the cross section 21b on the display unit 15 is z2, and the Z position of the stage 10 corresponding to the z2 is Z2. Also, the z-coordinate of the cross section including the point specified by the user (the cross section expressed by a dashed line) on the display unit 15 is z3, and the Z position of the stage 10 corresponding to z3 is Z3.

According to the above condition, Z3 as the cross section position to be obtained is given by the following equation.

$$Z3 = Z1 + (Z2 - Z1)/(z2 - z1)*(z3 - z1)$$

Thereby, the Z position of the stage 10 corresponding to the point specified by the user is obtained, and the cross section position thereof is determined.

Additionally, in the present embodiment, a component which emits pulsed laser beam can be used as the laser light source 1 for exciting the 3-D specimen 9 so that the specimen emits fluorescence due to multiphoton excitation. Because multiphoton excitation is caused only on the focal plane which the laser beam is concentrated, it is possible to irradiate the focal plane alone by the excitation light for photostimulation and photobleaching. Also, when a pulsed laser beam is employed for the excitation, laser beam with a longer wavelength than in the case of the CW (continuous wave oscillation) laser beam can be used so that excitation can be caused at a deeper position than the ordinary (CW) laser beam can reach, accordingly, the pulsed laser beam is advantageous for the observation and the implementation of the photostimulation/photobleaching of specimens which are large in the focal direction such as a nerve cell in which the tissue and the axon have developed for example. Further, the excitation by multiphoton excitation is caused only on the focal plane on which the energy density becomes so high so that photostimulation and photobleaching can be caused only at the desired site.

Embodiment 2

Figure 8:
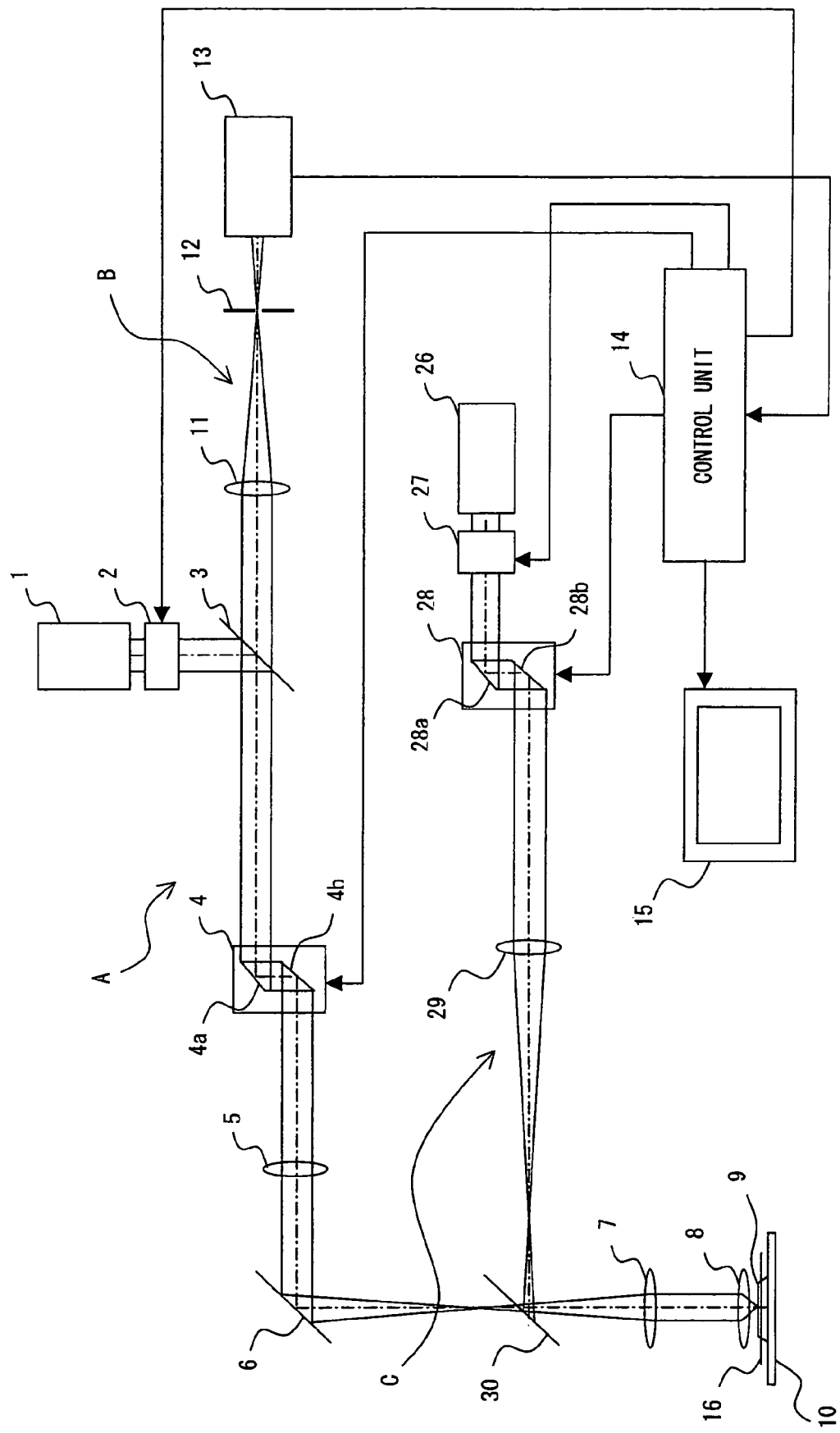
FIG. 8 shows a configuration of the confocal laser microscope device as a confocal observation system according to an embodiment 2.

FIG. 8 shows a configuration of a confocal laser microscope device as a confocal observation system according to an embodiment 2 of the present invention.

In FIG. 8, the differences from the configuration in FIG. 1 are that the present configuration further comprises a laser light source 26 for emitting an irradiating laser beam, a laser control unit 27 for adjusting the wavelength and intensity of the laser beam emitted by the laser light source 26, an optical scanning unit 28 for deflecting the laser beam in the directions of two-dimensions (X and Y directions) which includes two optical scanners 28a and 28b, a relay lens 29, a dichroic mirror 30, and that the internal configuration of the control unit 14 is slightly different from that in FIG. 1 because of the above additional components. Except for the above, the configuration is the same with that in FIG. 1.

Note that in the present device, the optical system comprising the laser light source 26, the laser control unit 27, the optical scanning unit 28 and the relay lens 29 is referred to as the scanning optical system C.

In the device according to the present embodiment, the laser beam emitted from the laser light source 26 is adjusted to a laser beam having an arbitrary wave length and intensity by the laser control unit 27 controlled by the control unit 14, thereafter, is guided to the optical scanning unit 28 controlled by the control unit 14, and is deflected in an arbitrary direction. The laser beam which has been deflected is transmitted through the relay lens 29, thereafter, is synthesized with the light from the scanning optical system A by the dichroic mirror 30, and the focal plane 16 of the 3-D specimen being transmitted through the imaging lens 7 and the objective lens 8 is irradiated.

Figure 9:
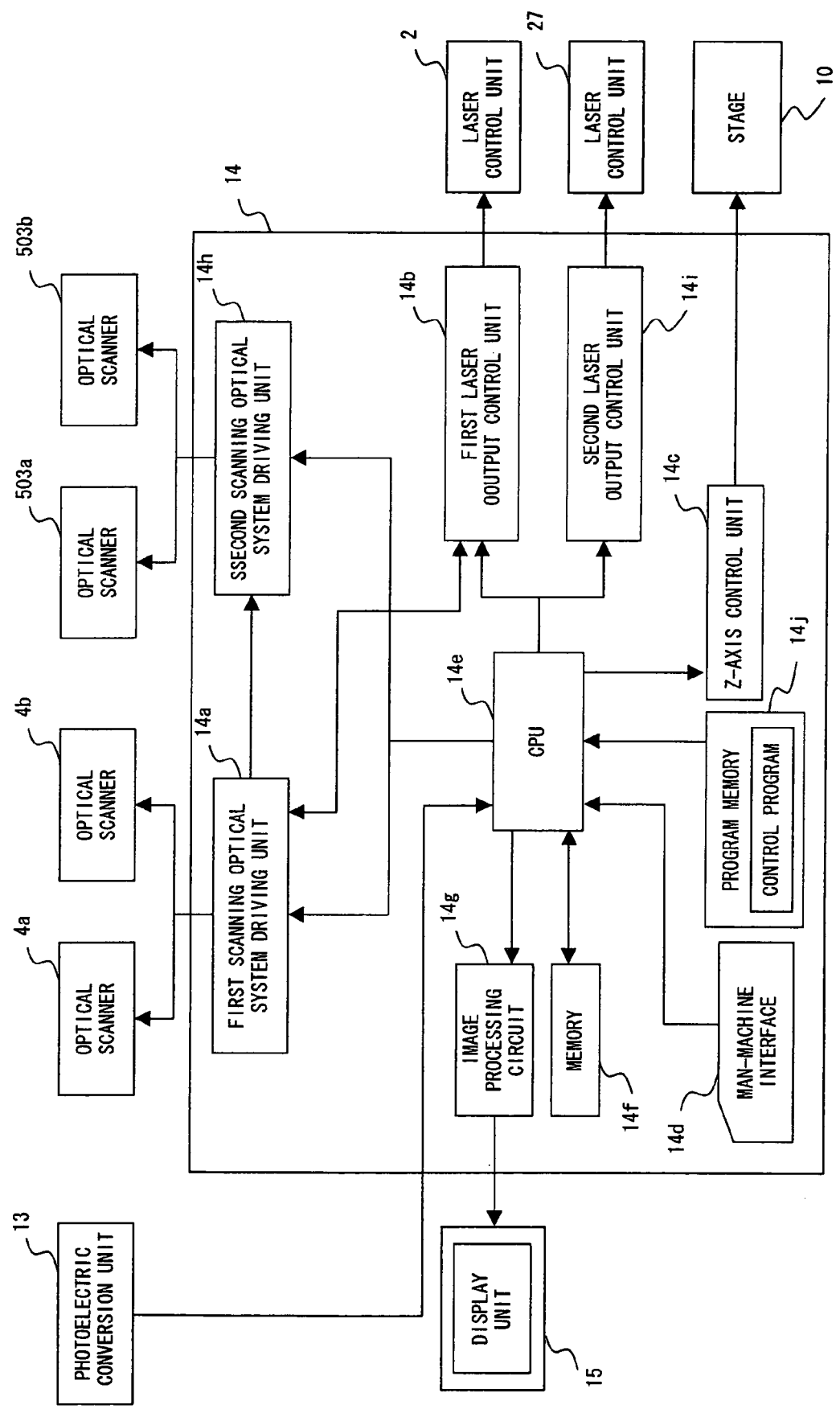
FIG. 9 is a block diagram for showing a configuration of a control unit according to the embodiment 2.

FIG. 9 is a block diagram showing the configuration of the control unit 14 according to the present embodiment.

In FIG. 9, the difference from FIG. 2 is that the configuration further comprises a second scanning optical system driving unit 14h for driving the optical scanners 28a and 28b, a second laser output control unit 14i for controlling the laser control unit 27. As a result of this configuration, the laser beam from the laser light source can be made to irradiate a desired position by controlling the drive of the optical scanning unit 28 and the laser control unit 27. Also, the first scanning optical system A and the second scanning optical system C can be both controlled separately or synchronously as occasion demands. Except for the above, the configuration is the same with that in FIG. 2.

The operation of the confocal laser microscope according to the present embodiment is the same as that of the device according to the embodiment 1 except for that in the present device, the irradiation of the 3-D specimen 9 by the excitation light is executed not by the scanning optical system A but by the scanning optical system C. Specifically, in the present device, the scanning optical system A is used upon acquiring the optical cross sectional image, and the scanning optical system C is used upon irradiating the 3-D specimen 9 with the excitation light. However, in the present device, the irradiation position of the laser beam of the scanning optical system C is set to correspond to the irradiation position of the laser beam of the scanning optical system A in advance.

As above, according to the present embodiment, the irradiation of the 3-D specimen 9 by the excitation light and the acquisition of the optical cross sectional image can be separately executed so that the phenomenon which is caused in the 3-D specimen after the photostimulation and the photobleaching can be accurately measured in a real time.

Additionally, in the above described embodiments 1 and 2, the explanations have been given by using the scanning confocal laser microscope which includes a scanning optical system as means for acquiring an image, however, as means for acquiring the image, the disk scanning confocal microscope can also be used.

Also, in the above described embodiments 1 and 2, the confocal observation system according to the present invention has been applied to the confocal laser microscope device, however, the confocal observation system according to the present invention can be applied also to an endoscope system which requires a scanner unit for acquiring an image.

Also, in the above described embodiments 1 and 2, the cross sectional region in the three-dimensional region specified in the three-dimensional image of the 3-D specimen can be obtained regardless of the optical cross sectional images used for the construction of the three-dimensional image of the specimen.

Embodiment 3

Figure 10:
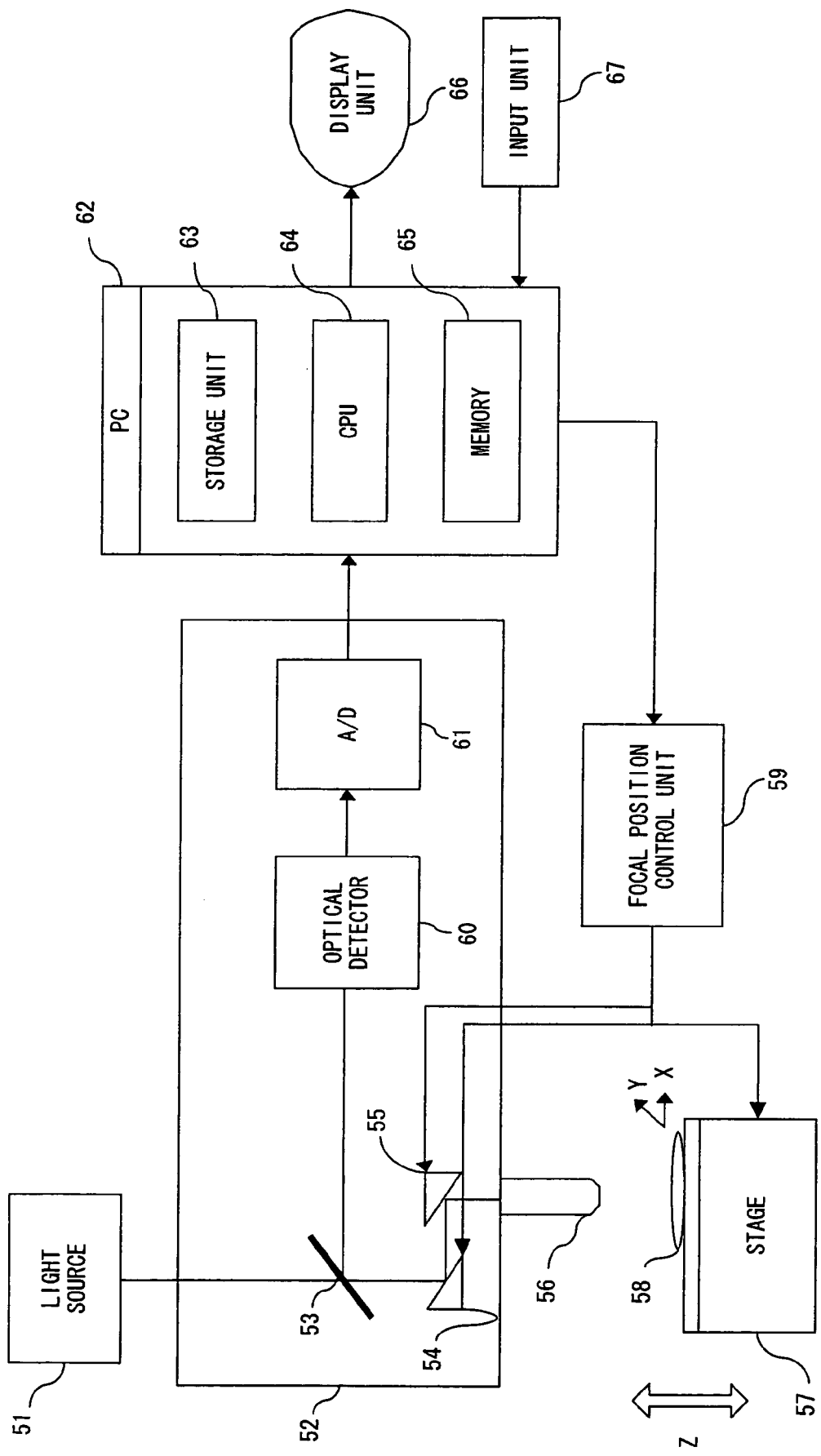
FIG. 10 shows an embodiment 3.

FIG. 10 shows a configuration of the confocal scanning microscope as a confocal observation system according to an embodiment 3. In FIG. 10, numeral 51 denotes a light source, and the laser beam emitted from the light source 51 is irradiated to the dichroic mirror 53 in a microscope body 52. The portion of the laser beam which has been transmitted through the dichroic mirror 53 is subject to position control by an X-direction scanner 54 and a Y-direction scanner 55, and is incident on an objective lens 56.

The laser beam incident on the objective lens 56 irradiates the focal position on a sample 58 on a stage 57 in accordance with the above position information. Then, the fluorescence is emitted.

In the above case, the stage 57 is subject to position control in the Z direction in accordance with the position information from the focal position control unit 59.

The focal position control unit 59 conducts control of the focal position using the position information from the above CPU 64, in which the position information of the X direction is output to the X-direction scanner 54, the position information of the Y direction is output to the Y-direction scanner 55, and the position information of the Z direction is output to the Z-direction scanner 57.

The fluorescence of the sample 58 reaches the dichroic mirror 53 along the same path as above and in the opposite direction, is reflected by the dichroic mirror 53, is concentrated on a confocal pinhole (not shown) by a confocal lens (not shown), and reaches an optical detector 60 via a confocal pinhole.

The optical detector 60 is connected to the CPU 64 of a PC 62 via an A/D converter 61. Specifically, the fluorescence emitted by the sample 58 is photoelectrically converted by the optical detector 10, and the electric signal which depends upon the intensity of the fluorescence is input to the A/D converter 61. The A/D converter 61 converts the above electric signal to a digital data signal, and transmits the digital data signal to the PC 62.

The CPU 64 in the PC 62 forms a three-dimensional image in accordance with the digital data provided by the A/D converter 61, for example, based on the volume rendering which is one of the visualization methods for computer graphics and the like, sends the formed three-dimensional image data to a display unit 66, and displays the three-dimensional image of the sample 58 on the display unit 66.

The CPU 64 is also connected to an input unit 67 so that the CPU 64 displays a region of interest on the display unit 66 and stores the region of interest specified by the user in accordance with instructions from the input unit 67. In a storage unit 63, a computer program for controlling the operation of the microscope, specifying the region of interest within the three-dimensional image drawn on the display unit 66, and determining the scanned region based on the region of interest is stored.

Also, in memory 65, a three-dimensional image generated by the CPU 64 and the scan conditions regarding the region of interest are stored.

As the CPU 64, the memory 65, the storage unit 63 and the like, a commonly used personal computer can be used. The process to be described later can be executed by a computer program, and the processing program is stored in a CD-ROM, a hard disk or the like as a storage medium.

And, as needed, the above processing program is read out of the media and into the memory of the above personal computer, and the process is executed by the CPU so that respective devices connected to the personal computer are controlled.

Figure 11:
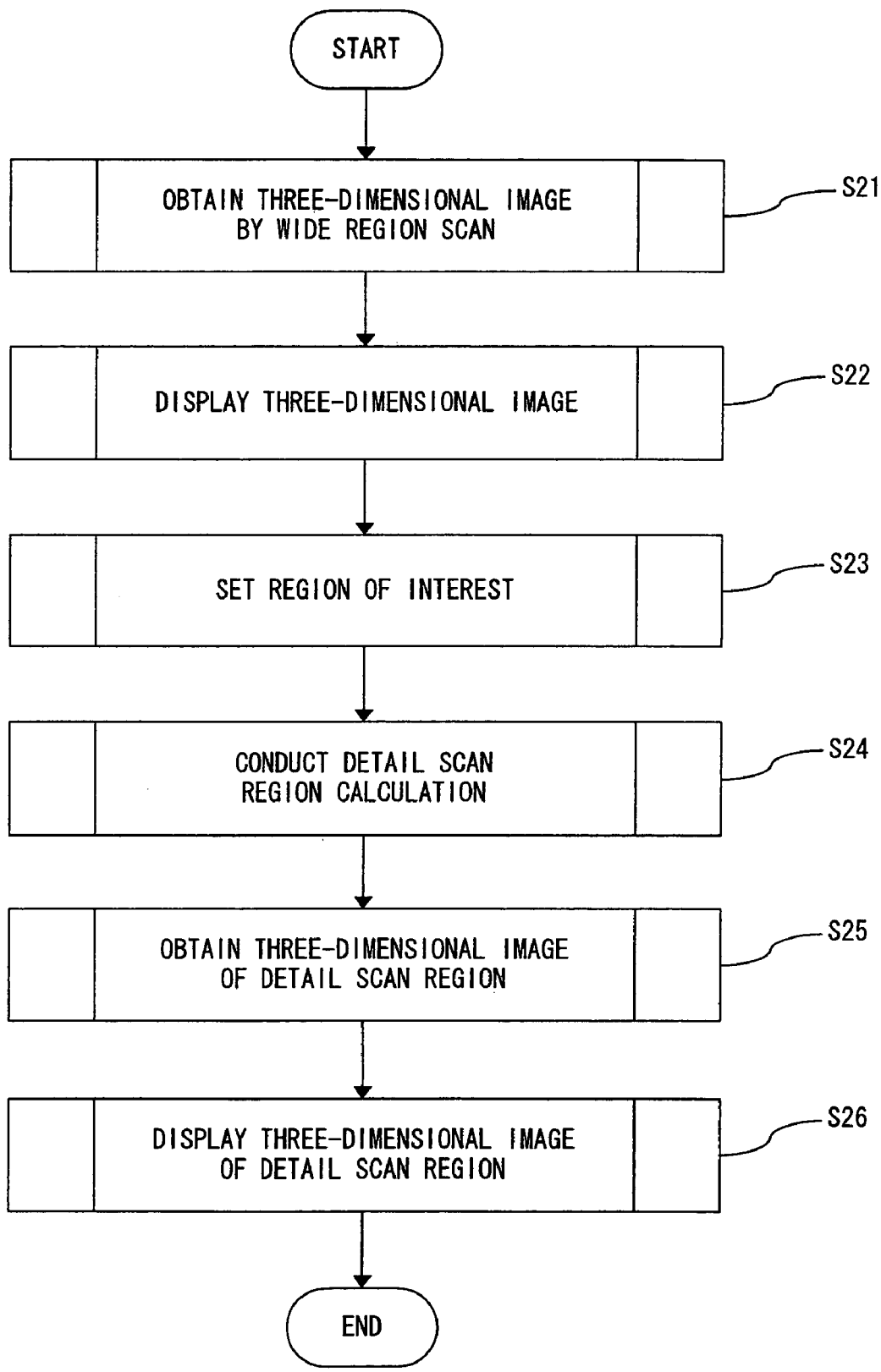
FIG. 11 is a flowchart for explaining the operations in the embodiment 3.

The processes of the above configuration in the present embodiment will be schematically explained by referring to FIG. 11.

First, in a step S21, a wide region is scanned and a Z-stack image for the scanned wide region is acquired in order to perceive the entirety of the specimen. Upon this, the amount of used memory and the scanning time can be reduced by scanning at a lower resolution. Next, in a step S22, the three-dimensional display image of the specimen is constructed on the PC 62 based on the Z-stack image for the wide region obtained in the step S21, and the constructed image is displayed on the display unit 66. Then, in a step S23, the user specifies the region of interest in the three-dimensional image displayed on the display unit 66.

In a step S24, a detail scan region calculation is conducted based on the region of interest specified in the step S23, and the position information of the detail scan region and the scan conditions are stored in the memory 65 of the PC 62.

In a step S25, the Z-stack image regarding the above region of interest is obtained by again scanning the specimen over the detail scan region based on the information of the detail scan region stored in the memory 65.

In a step S26, a three-dimensional display image is constructed from the Z-stack image obtained in the step S25, and is displayed on the display unit 66 as a three-dimensional image.

Next, each step in the flowchart of FIG. 11 is specifically explained. First, in the step S21 in FIG. 11, the Z-stack image for the wide region is obtained. Next in the step S22, the process for constructing a three-dimensional image from the Z-stack image and displaying the three-dimensional image is executed.

Figure 12:
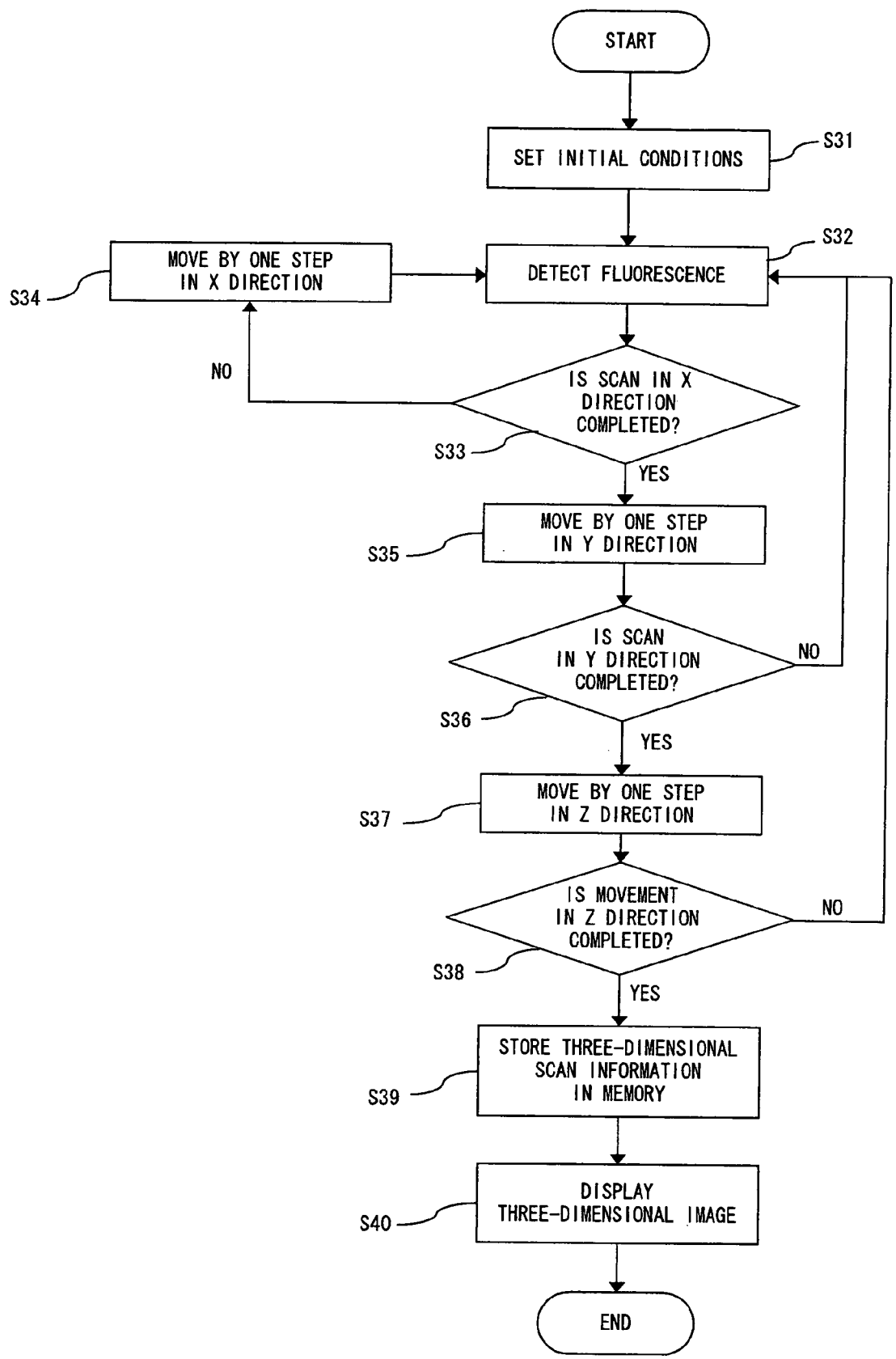
FIG. 12 is a flowchart for explaining the operations for acquiring the Z-stack image in the embodiment 3.

The process of the steps S21 and S22 will be explained by referring to FIG. 12.

First, in a step S31, the initial position information in the X, Y and Z directions is set in the focal position control unit 59. In accordance with the above set position information, the X-direction scanner 54, the Y-direction scanner 55 and the stage 57 move to a wide region scan start position which is the initial position. Next, in a step S32, a laser beam is output by the light source 51, the laser beam irradiates the sample 58, and fluorescence emitted by the sample 58 is detected. The detected data of the fluorescence is sent to the PC 62 via the optical detector 60 and the A/D converter 61 as previously described.

Next, in steps S33 and S34, the laser beam irradiates the sample 58 while the X-direction scanner 54 is moved in the X direction by one step until the scan in the X direction is completed. The fluorescence emitted by the sample 58 is sequentially detected by the optical detector 60 and the detected data is transmitted to the PC 62.

When the scan in the X direction is completed, the Y-direction scanner 55 is moved in the Y direction by one step in step S35, and it is determined whether or not all the scans in the Y direction are completed.

Then, the detection process of the above fluorescence is repeated until the scan in the Y direction is completed, and when the scan in the Y direction is completed, a two-dimensional sliced image is obtained. Thereafter, the stage 57 is driven to move one step in the Z direction by step S37.

When the stage 57 is moved one step in the Z direction it is determined whether or not the movement in the Z direction is completed by step S38, and when the result is No, the processes of the steps S32 to S37 are executed again.

When the scan in the Z direction is completed, the information input to the PC 62 is stored in the memory 65 in a step S39. Upon this, focal position information P_end at the time of the completion of the wide region scan is stored in the memory 65 together with the fluorescence information of the sample.

In a step S40, the CPU creates the three-dimensional image by a three-dimensional construction based on the information (Z-stack image) stored in the memory 65, and displays the created image on the display unit 66.

The Z-stack image here is a bundle of the plurality of the two-dimensional sliced images obtained for each individual step of the movement of the stage in the Z direction, superimposed in the optical axis direction.

Figure 13:
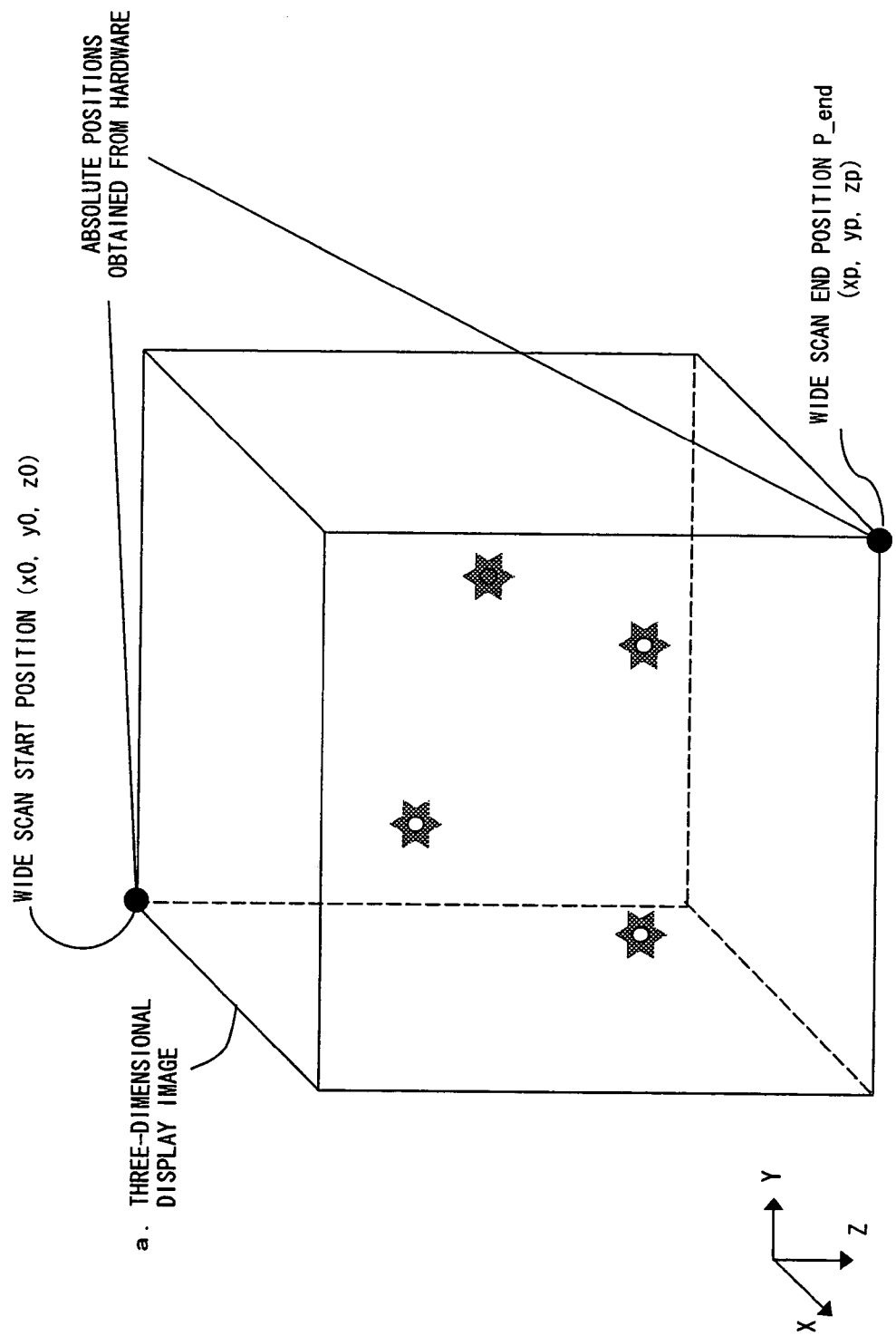
FIG. 13 shows the three-dimensional image obtained by a three-dimensional construction process from the Z-stack image obtained in the Z-stack image acquisition process according to the embodiment 3.

FIG. 13 shows an example of the three-dimensional image of the sample 58 obtained in the above process. The X axis in FIG. 13 expresses the X axis direction in the specimen, and corresponds to the scanning direction of the X-direction scanner 54 operated based on the position information in the X direction output by the focal position control unit 59. Similarly, the Y axis in FIG. 13 expresses the Y axis direction in the specimen, and corresponds to the scanning direction of the Y-direction scanner 55 operated based on the position information in the Y direction output by the focal position control unit 59.

The Z axis in FIG. 13 expresses the Z axis direction in the specimen, and corresponds to the movement. direction of stage 57 operated based on the position information in the Z direction output by the focal position control unit 59.

Further, along all the axes in the three-dimensional image displayed on the display unit 66, the relative coordinate values from the wide region scan start position which is the origin are displayed, and the size of each axis can be expressed similarly to the scanned distance in the scanned region in the direction of the corresponding axis (X axis, Y axis and Z axis). Specifically, when a 20 nm scan is executed in to be noted that the manner of the display is not limited to 20 nm is displayed on the image. Additionally, it is to be noted that the manner of the display is not limited to the above, and any manner of display that can accurately display the three-dimensional image can be employed. For example, a scale can be marked on each axis, or the coordinate values of a point specified by the user with a mouse or the like can be expressed.

Additionally, the initial position information in the above X axis direction, Y axis direction and Z axis direction is expressed by (x0, y0, z0) and serves as the wide scan start position. The above described P_end is expressed by (xp, yp, zp) as the wide scan end position.

The above values of (x0, y0, z0) and (xp, yp, zp) correspond to the absolute positions obtained from the hardware.

Additionally, any manner of construction and display of the image expressed based on the wide scan executed in the step S21 can be employed as long as the three-dimensional shape of the specimen can be confirmed by the constructed and displayed image.

Next, the setting of the region of interest in the step S23 of FIG. 11 will be specifically explained. In this step, the region of interest is drawn in the three-dimensional display image "a" obtained in the step S22. Specifically, the region to be scanned in detail is set in the wide three-dimensional image.

In the present example, an example in which two regions of interest are drawn is shown. The number and the size of the specified regions of interest can be arbitrarily selected.

Additionally, the example in which the region of interest is specified by a mouse of the computer as the input unit 67 connected to the PC 62 is shown, however, the means of the specification is not limited to the means of using a mouse, and various other means for specifying the region of interest can be employed.

Figure 14:
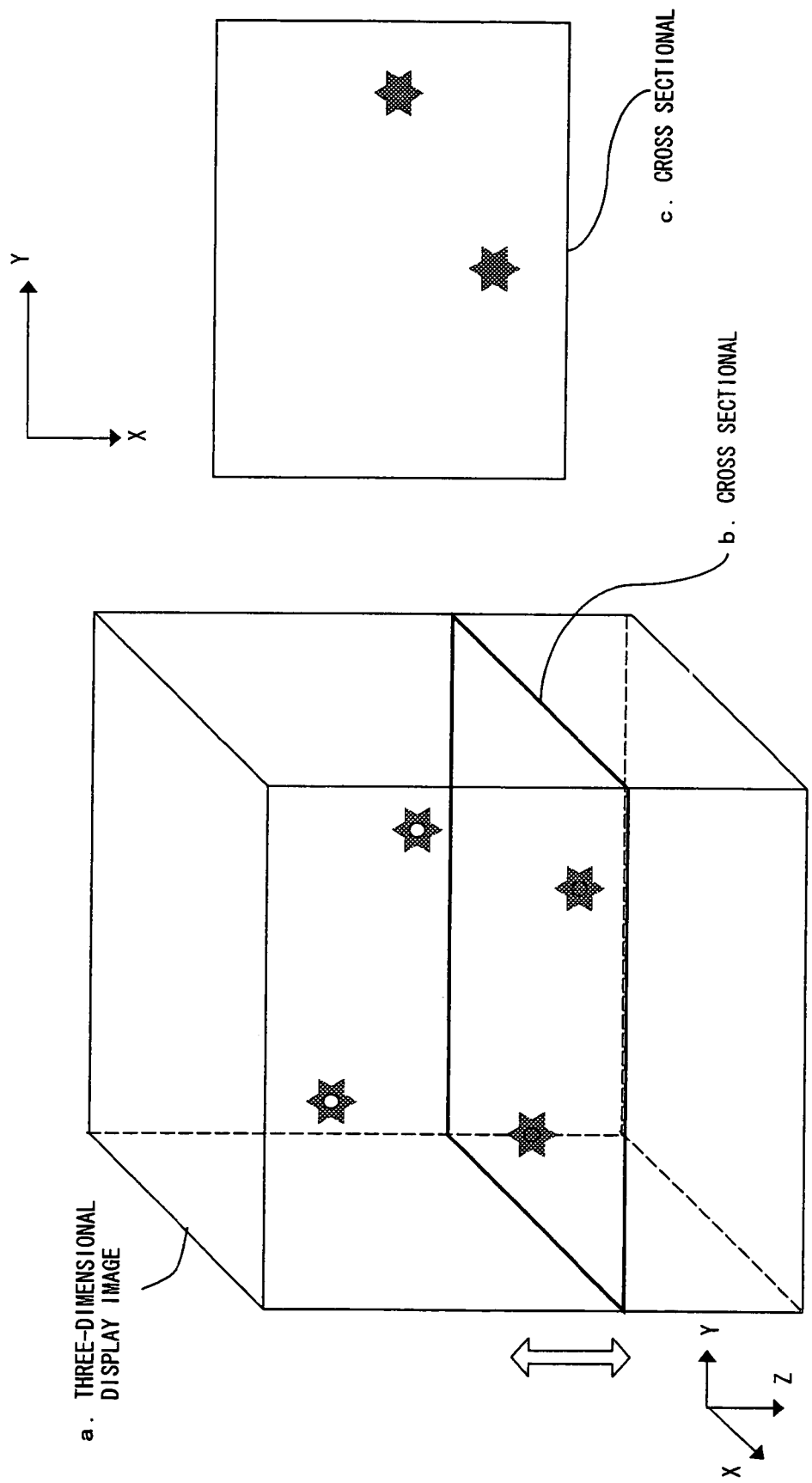
FIG. 14 shows an example of setting regions of interest in the embodiment 3.

For example, when a cross section "b" which is parallel to the XY plane is specified by a mouse in the three-dimensional display image displayed in the step S22 shown in FIG. 14, the intensity information of the position at which the cross section "b" crosses the three-dimensional display image "a" is displayed as a cross sectional view "c".

Thereby, the observer as the above user can search the region of interest while moving the cross section "b" with the mouse connected to the PC 62.

Next, the observer draws a region of interest "d" (see FIG. 15) on the cross sectional view "c" displayed on the display unit 66 with a mouse. The region of interest can be of an arbitrary shape such as rectangular, circular or the like. In this example, the case of a rectangular region is explained.

The position information of the region of interest is transmitted to the CPU 64, and is converted to the position information of the three-dimensional display image "a" stored in the memory 65. Based on this position information, the CPU 64 displays a region of interest "e" (three-dimensional region) having a predetermined depth in the Z direction as an initial region of interest (three-dimensional region) in the three-dimensional display image "a" displayed on the display unit 66.

Figure 15:
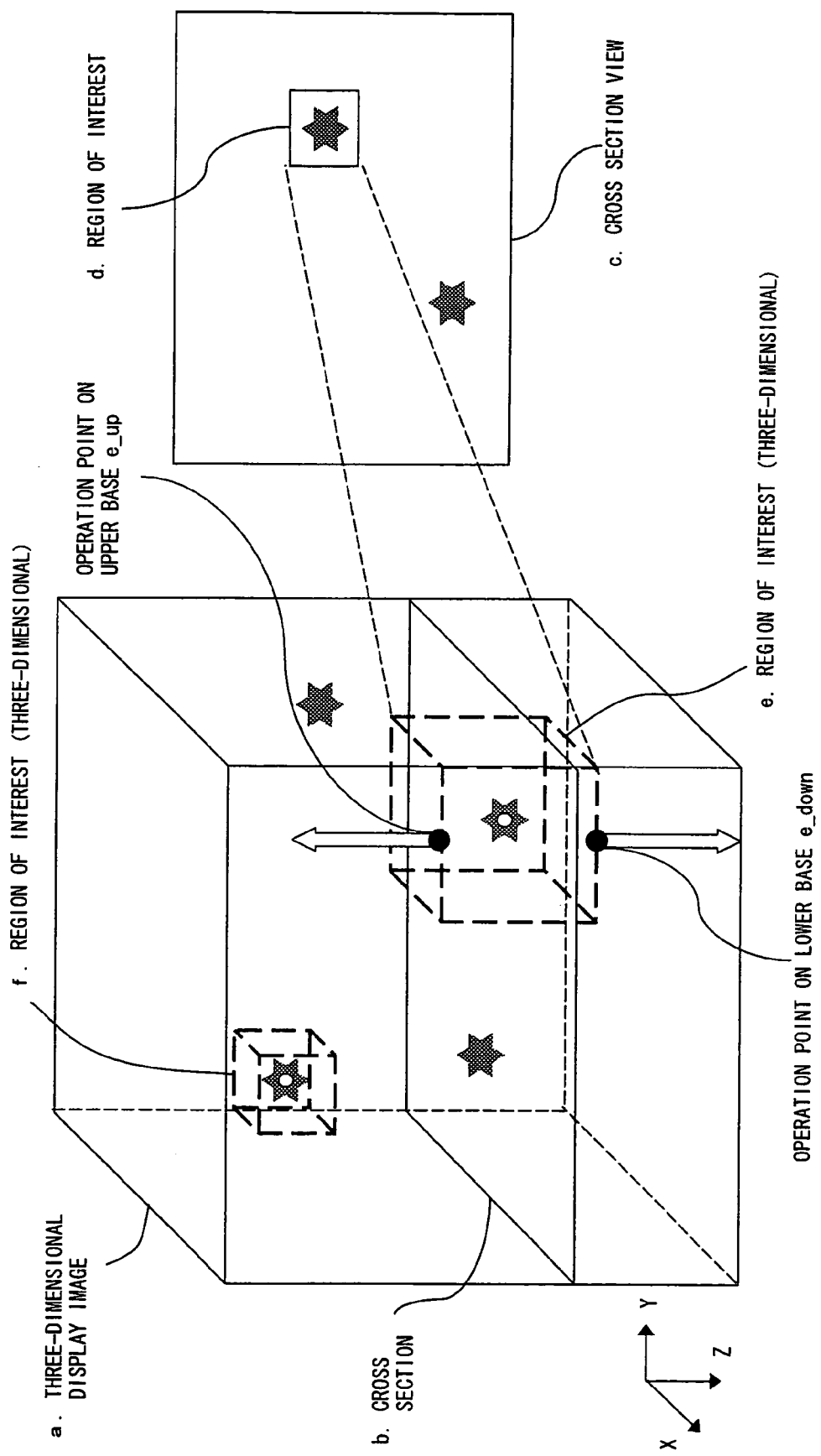
FIG. 15 shows an example of setting regions of interest in the embodiment 3.

When the depth of this region of interest "e" in the Z direction is to be changed for example, the observer moves an operation point on the upper base e_up, an operation point on the lower base e_down and the like in the region of interest "e" in FIG. 15 by dragging a mouse pointer in the upper and lower directions, thereby, the region of interest can be extended and reduced. The data regarding the region of interest after a change such as the above is stored in the memory 65 after each change. Additionally, as the information to be stored regarding the region of interest, the scan information such as the number of scans in the X direction, the number of scans in the Y direction, the number of slices in the Z direction, the sampling wavelength employed when scanning the region of interest and the like can be stored in association with one another together with the above data regarding the region of interest.

A region of interest "f" in FIG. 15 can be additionally drawn as another region of interest in the three-dimensional display image "a" by conducting the above operations again.

Next, the detail scan region calculation in the step S24 in FIG. 11 will be explained. Hereinafter, as a representative example, the detail scan region calculation regarding the above explained region of interest "e" will be explained excluding the above additional region of interest, by using FIG. 16 which focuses on the region of interest "e".

The scan start position in the region of interest "e" is obtained in the manner explained in the step S23. And the scan start position "i" and the scan end position "j" of the region of interest "e" in the three-dimensional display image "a" stored in the memory 65 are used.

Figure 16:
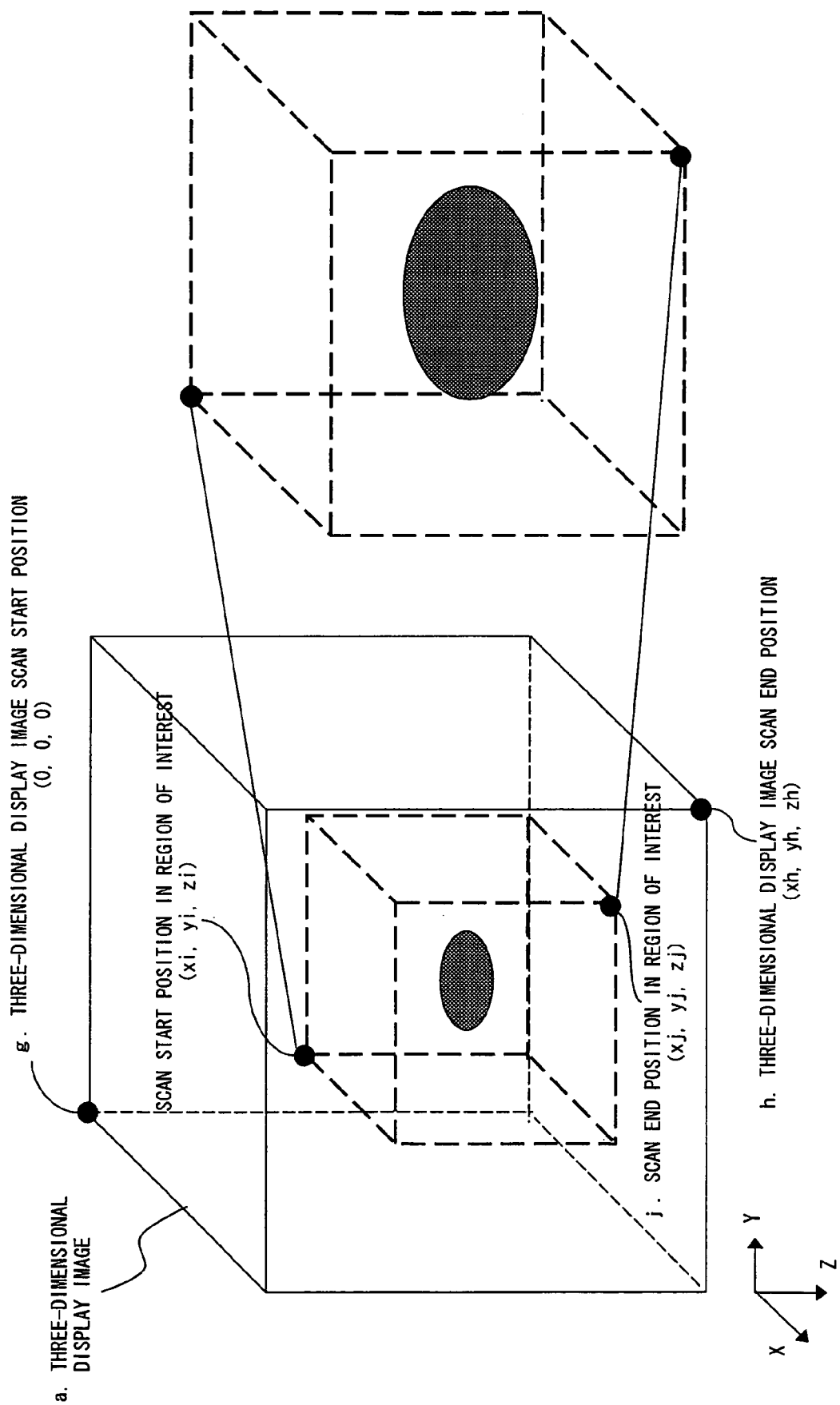
FIG. 16 explains the positional relationship between the three-dimensional image obtained by the wide scan and the region of interest in the embodiment 3.

In FIG. 16, in the calculation for setting the focus of the laser beam on the scan start position in the region of interest "e", a three dimensional display image scan start position "g" (0, 0, 0) (corresponding to the scan start position (x0, y0, z0) upon acquiring the three-dimensional display image "a") and a three dimensional display image scan end position "h" (xh, yh, zh) (corresponding to the scan end position (xp, yp, zp) upon acquiring the three-dimensional display image) are used. Specifically, based on the relationship between the three dimensional display image scan start position "g" and the three dimensional display image scan end position "h", the vector Vh to the scan start position "i" in the region of interest "e" is calculated. The above vector Vh is expressed by the equation (1) and is the relative position from the three dimensional display image scan start position "g".

$$Vh = i - h \tag{1}$$

Also, the scan end position information P_end upon acquiring the three-dimensional display image and the current laser beam focal position P are stored as the absolute positions obtained from the hardware accordingly, the motion vector V to the scan start position "i" in the region of interest "e" can be obtained by the following equation (2) utilizing the equation (1). Based on V obtained by the equation (2), the focus of the laser beam can be moved to the scan start position in the region of interest.

$$V = (P\_end - P) + (i - h) \tag{2}$$

Next, in order to control the scanning width in the X axis, Y axis and Z axis directions in scanning the region of interest "e", variation of the electric signals for controlling the operations of the X-direction scanner 54, the Y direction scanner 55 and the stage 57 are set.

For example, in FIG. 17, from the number of pixels, W, in the X axis direction in the three-dimensional display image, the number of pixels, H, in the Y axis direction, the number of pixels, S, in the X axis direction in the region of interest "e" in the three-dimensional display image and the number of pixels, T, in the Y axis direction, S/W is recognized as the variation in the X axis direction, and (S/W)*(T/H) is recognized as the variation in the Y axis direction. Because, the voltage width Vx for controlling the scan in the X direction and the voltage width Vy for controlling the scan in the Y direction upon acquiring the three-dimensional display image "a" are stored in the memory 65, voltage width V'x and voltage width V'y respectively for controlling the scan in the X direction and the scan in the Y direction upon the detail scan are obtained by the following equation (3).

$$V'x = Vx*(S/W)$$

$$V'y = Vy*(S/W)*(T/H) \tag{3}$$

Similarly, from the number of pixels, D, in the Z axis direction in the three-dimensional display image "a", the number of pixels, u, in the Z axis direction of the region of interest "e" and a voltage phase Vz for controlling the stage 57 upon acquiring the three-dimensional display image "a", voltage width V'z for controlling the stage 57 upon the detail scan is obtained from the following equation (4).

$$V'z = Vz*(u/D) \tag{4}$$

Further, from the number of samples, n, in the Z direction (the number of the slices in the Z axis direction) stored in the memory 65 and a distance Dz in the Z distance in the region of interest, the distance of the movement of the stage for one step Dz/n is calculated.

Further, it is also necessary to move the center position upon scanning, therefore, the position information from the scan center position upon acquiring the three-dimensional display image "a" to the center position in the region of interest "e" is obtained. The above obtained calculation result information (data such as the number of scans in the direction of each axis, the scanning width along each axis, and the like) is stored in the memory 65, and the scan region calculation process for the region of interest "e" is ended.

The case where there is a plurality of regions of interest is explained. For example, when there is an additional region of interest "f", the above process is also executed for the region of interest "f", and the detail scan region of the region of interest "f" is obtained.

Figure 18:
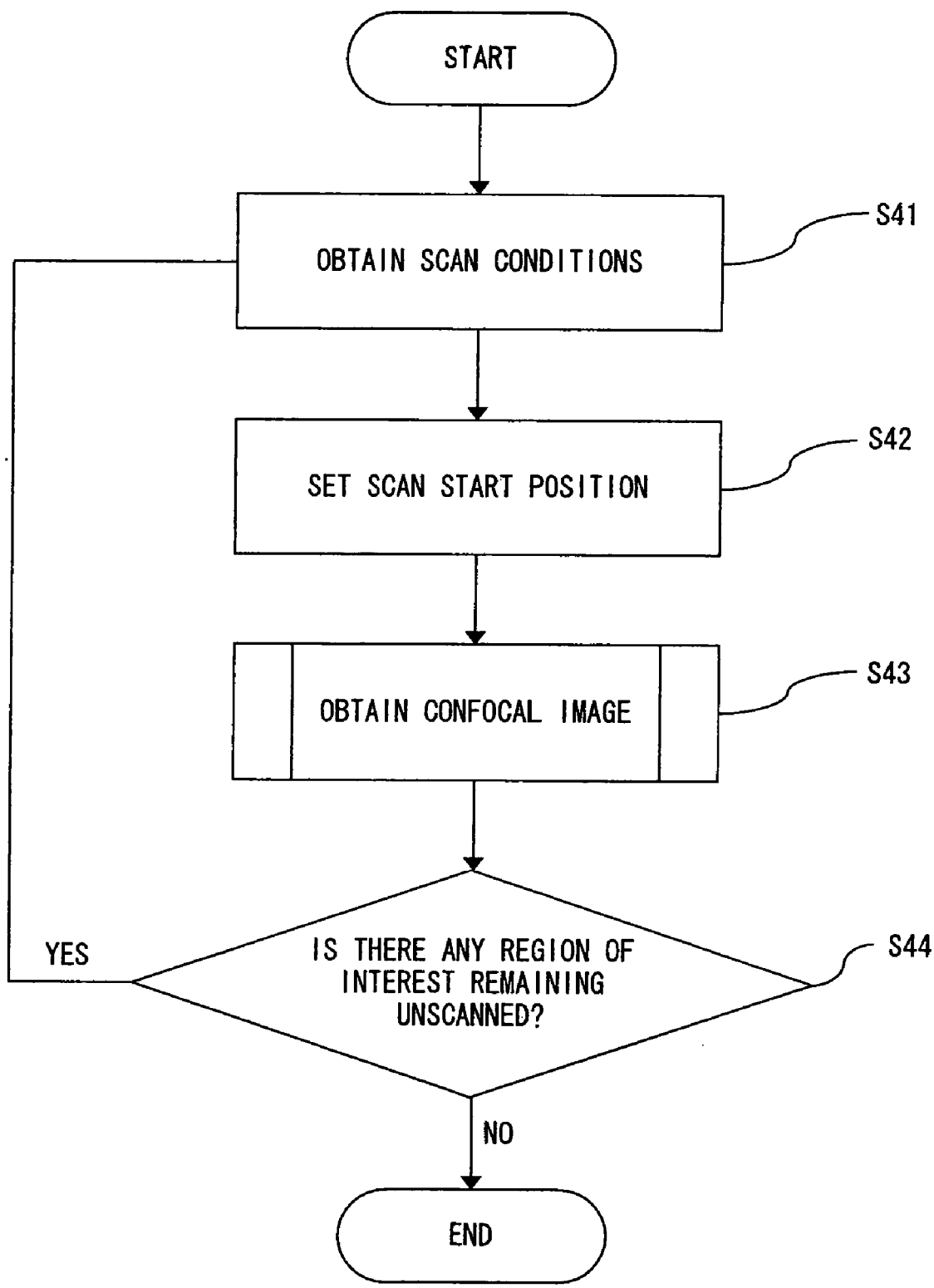
FIG. 18 is a flowchart explaining the acquisition of the Z-stack image by the detail scan region in the embodiment 3.

Next, processes of the detail scan in the steps S25 and S26 in FIG. 11 are specifically explained by referring to FIG. 18.

First, in a step S41, the scan conditions calculated by the detail scan region calculation in the step S24 in FIG. 11 are read from the memory 65.

In the present embodiment, explanation is given for the case where the scan conditions first read from the memory 65 are for the region of interest "e", however, the order of reading the scan conditions can be arbitrarily selected.

Next, in a step S42, the read scan conditions for the region of interest "e" are transmitted to the focal position control unit 59 by the CPU 64. The focal position control unit 59 transmits the scan start position information to the X-direction scanner 54, the Y-direction scanner 55 and the stage 57.

The X-direction scanner 54, the Y-direction scanner 55 and the stage 57 are moved to the input scan start position. In a step S43, the scan is conducted for the region of interest "e" in the sample 58, the three-dimensional information of the region of interest "e" is obtained, and the obtained information is stored in the memory 65.

Upon this, the number of scans in the direction of each axis (x, y and z axes) is the number obtained by the above detail scan region calculation, and is separated and independent of the number of the scans for the three-dimensional display image "a". In other words, because the three-dimensional display image obtained by the wide region scan can be for the purpose of a preview function, a large number of scans therefor is not needed. However, in the scan of the region of interest, the region of interest is scanned in detail so that the number of the scans of the region of interest is not always the same as the number of the scans for the wide region scan. Specifically, the scan of the region of interest is conducted at a higher resolution than that of the wide region scan.

Next, in a step S44, it is determined whether or not there is a region of interest which remains un-scanned. In the present embodiment, there is the region of interest "f" remaining un-scanned so that the process returns to the step S41 and the scan conditions for the region of interest "f" are read from the memory 65. The read scan conditions are again transmitted to the focal position control unit 59, and the next scan start point information is set respectively in the X-direction scanner 54, the Y-direction scanner 55 and the stage 57. Thereafter, the above detail scan is conducted for the region of interest "f", and when the three-dimensional information regarding all the regions of interest is obtained, the detail scan is completed.

As a result of the above method, the detail scan can be executed for the plurality of the regions of interest specified by the observer. Accordingly, the observer can set the three dimensional regions of interest intuitively.

Additionally, in the above configuration, the movement in the Z direction is realized by the movement of the stage 57, however, the above movement in the Z direction can be realized by the movement of the objective lens.

Further, in the above embodiment, the XY plane (two-dimensional region) is employed as the cross section serving as the reference for setting the region of interest, however, cross sections in arbitrary directions such as the YZ plane, the XZ plane or the like can be employed. Further, the three-dimensional region of interest can be specified in the space without using any cross section. Still further, a point whose surrounding space is specified as the region of interest can be employed.

Further, in the present embodiment, a laser beam of a single wavelength is used as the laser beam from the light source 51, however, a plurality of laser light sources can be used. In this case, high intensity information of a plurality of targets can be obtained.

In addition, the present embodiment has been explained for the case of the confocal scanning microscope, however, the present invention can be applied also to the confocal scanning microscope of a type other than the type used in the embodiment, without departing from the spirit of the present invention.

As above, according to the present invention, the user observes the specimen which is displayed as the three-dimensional image displayed as the preview image so that the user can recognize the region of interest as the three-dimensional image for a detail observation and can easily specify the region of interest in the 3-D image. Further, the user can change the manner of specifying the three-dimensional scan region so that the user can specify the three-dimensional region to be observed easily and intuitively. Still further, the three-dimensional image is constructed and displayed based on the obtained three-dimensional information so that the user can observe the sample easily and in detail.

Also, the user can set the portion to be observed by using a point, a two-dimensional region or a three-dimensional region so that the user can easily specify the observation region surrounding the set point/region.

Hereinabove, the present invention has been explained in detail, however, the scope of the present invention is not limited to the above embodiments, and it is naturally understood that various modifications and alternations can be allowed within the spirit of the present invention.

For example, in the above configurations and/or operations explained in each of the above embodiments 1 to 3, a part or the whole of the configurations and/or operations explained in one embodiment can also be applied to the other embodiments.

As explained above, according to the present invention, by specifying arbitrary three-dimensional regions in the three-dimensional image of the specimen, photostimulation and photobleaching can be accurately conducted on the corresponding region in the specimen. Also, the behavior analysis after photostimulation of the specimen having a three-dimensional structure can be accurately conducted.

Also, according to the present invention, the user can three-dimensionally observe the observation targets which are scattered in the space of the biological sample or the like by previewing the biological sample in the three-dimensional image. Also, upon the detail observation, the plurality of the three-dimensional regions of interest are recognized three-dimensionally so that the specification of the regions of interest can be conducted three-dimensionally. Further, the user can change the manner of specifying the three-dimensional scan region, and can specify the three-dimensional scan region of interest easily and intuitively so that the time consumed for setting the three-dimensional scan region can be reduced. Still further, while setting the three-dimensional scan region there is no laser beam irradiation, so that damage to the sample caused by laser beam irradiation can be suppressed.

What is claimed is:

1. A confocal observation system, comprising:
   an image acquisition unit for acquiring respective optical cross sectional images of a three-dimensional specimen at a plurality of different Z positions;
   a three-dimensional image construction unit for constructing a three-dimensional image from a set of the optical cross sectional images acquired by the image acquisition unit;

a display unit for displaying the three-dimensional image constructed by the three-dimensional image construction unit;

a specification unit for specifying at least one three-dimensional region in the three-dimensional image displayed on the display unit; and a region acquisition unit for acquiring a set of cross sectional regions corresponding to the at least one three-dimensional region specified by the specification unit, wherein the specified three-dimensional region is at least one of observed and stimulated by irradiating the set of cross sectional regions acquired by the region acquisition unit with at least one of excitation light and stimulation light.

2. The system according to claim 1, wherein:
the region acquisition unit acquires the set of cross sectional regions from the optical cross sectional images acquired by the image acquisition unit and/or by interpolation from the optical cross sectional images acquired by the image acquisition unit.

3. The system according to claim 1, wherein:
the excitation light and the stimulation light comprise a pulsed laser beam for exciting the three-dimensional specimen by multiphoton excitation.

4. The system according to claim 1, wherein:
the image acquisition unit comprises a first optical system for acquiring the optical cross sectional images of the three-dimensional specimen, and a second optical system is provided for irradiating the set of cross sectional regions acquired by the region acquisition unit with the excitation light or stimulation light.

5. The system according to claim 1, wherein:
the specification unit specifies a plurality of three-dimensional regions in the three-dimensional image displayed on the display;

the region acquisition unit acquires the set of cross sectional regions to be irradiated based on the plurality of the three-dimensional regions specified by the specification unit; and the set of cross sectional regions are scanned at a high resolution by the irradiation of the excitation light or the stimulation light.

6. The system according to claim 5, wherein:
the plurality of the three-dimensional regions are specified by the specification unit using a plurality of points specified in the three-dimensional image constructed by the three-dimensional image construction unit.

7. The system according to claim 5, wherein:
the plurality of the three-dimensional regions are specified by the specification unit using a plurality of two-dimensional regions specified in the three-dimensional image constructed by the three-dimensional image construction unit.

8. The system according to claim 5, wherein:
the plurality of the three-dimensional regions are specified by the specification unit using a plurality of three-dimensional regions specified in the three-dimensional image constructed by the three-dimensional image construction unit.

9. An irradiating method for a confocal observation system, comprising:
acquiring optical cross sectional images of a three-dimensional specimen;

constructing a three-dimensional image from the acquired optical cross sectional images;

specifying a desired three-dimensional region in the constructed three-dimensional image;

acquiring a set of cross sectional regions corresponding to the specified three-dimensional region; and irradiating the acquired set of cross sectional regions with at least one of excitation light and stimulation light.

10. A method of scanning for a confocal observation system, comprising:
acquiring optical cross sectional images of a three-dimensional specimen;

constructing a three-dimensional image from the acquired optical cross sectional images;

specifying a plurality of desired three-dimensional regions in the constructed three-dimensional image;

acquiring a set of cross sectional regions corresponding to the plurality of the specified three-dimensional regions; and scanning the acquired set of cross sectional regions at a high resolution by irradiation with at least one of excitation light and stimulation light.

11. A computer readable storage medium which stores a program for causing a computer to realize:
a function of acquiring optical cross sectional images of a three-dimensional specimen;

a function of constructing a three-dimensional image from the acquired optical cross sectional images;

a function of specifying a desired three-dimensional region in the constructed three-dimensional image;

a function of acquiring a set of cross sectional regions corresponding to the specified three-dimensional region; and a function of irradiating the acquired set of cross sectional regions with at least one of excitation light and stimulation light.

12. A computer readable storage medium which stores a program for causing a computer to realize:
a function of acquiring optical cross sectional images of a three-dimensional specimen;

a function of constructing a three-dimensional image from the acquired optical cross sectional images;

a function of specifying a plurality of desired three-dimensional regions in the constructed three-dimensional image;

a function of acquiring a set of cross sectional regions corresponding to the plurality of the specified three-dimensional regions; and a function of scanning the acquired set of cross sectional regions at a high resolution by irradiation with at least one of excitation light and stimulation light.

* * * * *